US010617689B2

(12) United States Patent
Cohen et al.

(10) Patent No.: US 10,617,689 B2
(45) Date of Patent: Apr. 14, 2020

(54) COMPOSITIONS, METHODS AND USES FOR THE TREATMENT OF DIABETES AND RELATED CONDITIONS BY CONTROLLING BLOOD GLUCOSE LEVEL

(71) Applicant: PHARNEXT, Issy les Moulineaux (FR)

(72) Inventors: Daniel Cohen, Saint Cloud (FR); Ilya Chumakov, Vaux le Penil (FR); Serguei Nabirochkin, Catenay Malabry (FR); Rodolphe Hajj, Saint Germain en Laye (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 15/142,227

(22) Filed: Apr. 29, 2016

(65) Prior Publication Data

US 2016/0235693 A1    Aug. 18, 2016

Related U.S. Application Data

(63) Continuation-in-part of application No. PCT/EP2014/073201, filed on Oct. 29, 2014.

(30) Foreign Application Priority Data

Oct. 30, 2013 (WO) ................. PCT/EP2013/072728
Apr. 30, 2014 (EP) ..................................... 14166734

(51) Int. Cl.
| | | |
|---|---|---|
| *A61K 31/437* | (2006.01) | |
| *A61K 31/55* | (2006.01) | |
| *A61K 31/122* | (2006.01) | |
| *A61K 31/216* | (2006.01) | |
| *A61K 31/53* | (2006.01) | |
| *A61K 31/4164* | (2006.01) | |
| *A61K 31/495* | (2006.01) | |
| *A61K 31/445* | (2006.01) | |
| *A61K 31/16* | (2006.01) | |
| *A61K 31/519* | (2006.01) | |
| *A61K 31/7004* | (2006.01) | |
| *A61K 31/197* | (2006.01) | |
| *A61K 31/138* | (2006.01) | |
| *A61K 31/137* | (2006.01) | |
| *A61K 31/44* | (2006.01) | |
| *A61K 31/422* | (2006.01) | |
| *A61K 31/155* | (2006.01) | |
| *A61K 31/42* | (2006.01) | |
| *A61K 31/135* | (2006.01) | |
| *A61K 31/196* | (2006.01) | |
| *A61K 31/24* | (2006.01) | |
| *A61K 31/4745* | (2006.01) | |
| *A61K 31/50* | (2006.01) | |
| *A61K 45/06* | (2006.01) | |

(52) U.S. Cl.
CPC .......... *A61K 31/519* (2013.01); *A61K 31/122* (2013.01); *A61K 31/135* (2013.01); *A61K 31/137* (2013.01); *A61K 31/138* (2013.01); *A61K 31/155* (2013.01); *A61K 31/16* (2013.01); *A61K 31/196* (2013.01); *A61K 31/197* (2013.01); *A61K 31/216* (2013.01); *A61K 31/24* (2013.01); *A61K 31/4164* (2013.01); *A61K 31/42* (2013.01); *A61K 31/422* (2013.01); *A61K 31/437* (2013.01); *A61K 31/44* (2013.01); *A61K 31/445* (2013.01); *A61K 31/4745* (2013.01); *A61K 31/495* (2013.01); *A61K 31/50* (2013.01); *A61K 31/53* (2013.01); *A61K 31/55* (2013.01); *A61K 31/7004* (2013.01); *A61K 45/06* (2013.01)

(58) Field of Classification Search
CPC .... A61K 31/155; A61K 31/44; A61K 31/519; A61K 31/197; A61K 31/196; A61K 31/16; A61K 31/138; A61K 31/135; A61K 31/42; A61K 31/55; A61K 31/4745; A61K 31/122; A61K 31/24; A61K 31/53; A61K 31/4164; A61K 31/495; A61K 31/7004
USPC ......................................................... 514/23
See application file for complete search history.

(56) References Cited

U.S. PATENT DOCUMENTS

| | | | |
|---|---|---|---|
| 5,019,591 A | | 5/1991 | Gardner et al. |
| 8,377,429 B2 * | | 2/2013 | Scannon ............... C07K 16/245 424/85.1 |
| 10,092,554 B2 * | | 10/2018 | Cohen .................. A61K 31/422 |
| 2003/0162754 A1 | | 8/2003 | Ligon |
| 2005/0024714 A1 | | 2/2005 | Hayashi et al. |

(Continued)

FOREIGN PATENT DOCUMENTS

| | | |
|---|---|---|
| EP | 1 884 513 | 2/2008 |
| GB | 2 432 526 | 5/2007 |

(Continued)

OTHER PUBLICATIONS

Glossary of medical education terms, Institute of International Medical Education. http://www.iime.org/glossary.htm Accessed in Mar. 2013. (Year: 2013).*

(Continued)

*Primary Examiner* — Yih-Horng Shiao
(74) *Attorney, Agent, or Firm* — Saliwanchik, Lloyd & Eisenschenk

(57) ABSTRACT

The present invention relates to compositions and methods for controlling glycaemia in a mammalian in need thereof. The present invention relates to compositions and methods for the treatment of diabetes disease and related disorders. More specifically, the present invention relates to novel therapies or combinatorial therapies of diabetes and related disorders, based on compositions controlling the blood glucose level.

20 Claims, 15 Drawing Sheets

(56) References Cited

U.S. PATENT DOCUMENTS

| | | |
|---|---|---|
| 2005/0025714 A1 | 2/2005 | Dugger, III |
| 2006/0004050 A1 | 1/2006 | Speicher et al. |
| 2008/0188457 A1* | 8/2008 | Barlow ............... A61K 31/155 514/212.06 |
| 2008/0213362 A1 | 9/2008 | Solomon |
| 2011/0046046 A1 | 2/2011 | Hara et al. |
| 2015/0231123 A1 | 8/2015 | Cohen et al. |

FOREIGN PATENT DOCUMENTS

| | | |
|---|---|---|
| WO | WO 2004/011003 | 2/2004 |
| WO | WO 2008/141189 | 11/2008 |
| WO | WO 2014/013025 | 1/2014 |
| WO | WO 2014/068007 | 5/2014 |

OTHER PUBLICATIONS

Arima et al. Positive Effect of Baclofen on Body Weight Reduction in Obese Subjects: A Pilot Study. Inter Med 49: 2043-2047, 2010. (Year: 2010).*

Anghinah, R., et al., "Effect of Baclofen on Pain in Diabetic Neuropathy," *Muscle & Nerve*, Aug. 1, 1994, vol. 17, No. 8, pp. 958-959.

Beales, P.E., et al., "Baclofen, a gamma-aminobutyric acid-b receptor agonist, delays diabetes onset in the non-obese diabetic mouse," *Acta Diabetologica*, Mar. 1, 1995, vol. 32, No. 1, pp. 53-56.

Crinquette, J.F., et al., "Une forme diffuse d'ectasie canaliculaire du pancréas?," *Gastroenterologie Clinique et Biologique*, Jan. 1, 1988, vol. 12, No. 11, pp. 866-867.

Database WPI, Week 199308, Jan. 19, 1993, Thomson Scientific, London, GB, AN 1993-061598, XP-002695548.

Dunn, C.J., et al., "Metformin: A Review of its Pharmacological Properties and Therapeutic Use in Non-Insulin-Dependent Diabetes Mellitus," *Drugs*, May 1, 1995, vol. 49, No. 5, pp. 721-749.

Egashira, N., et al., "Mexiletine Reverses Oxaliplatin-Induced Neuropathic Pain in Rats," *Journal of Pharmacological Sciences*, Jan. 1, 2010, vol. 112, No. 4, pp. 473-476.

Freyria, J., "Essai de la thérapeutique anti-ischémique dans le traitement des artériopathies de surcharge," *Gazette Medicale de France*, Jan. 1, 1975, vol. 82, No. 16, pp. 1989-1996.

Gomez, R., et al., "GABA Agonists Differentially Modify Blood Glucose Levels of Diabetic Rats," *Japanese Journal of Pharmacology*, Aug. 1, 1999, vol. 80, No. 4, pp. 327-331.

Hollenberg, N. K., et al., "Hyperkalemia in Diabetes Mellitus: Effect of a Triamterene-Hydrochlorothiazide Combination," *Archives of Internal Medicine*, Jun. 1, 1989, vol. 149, No. 6, pp. 1327-1330.

Langevin, J., et al., "Étude du tartrate d'ifenprodil dans le traitement des accidents vasculaires cérébraux aigus," *Quest-Médical*, May 20, 1976, vol. 29, pp. 853-854.

Lehnert, H., et al., "Controlled clinical trial investigating the influence of torasemide and flurosemide on carbohydrate metabolism in patients with cardiac failure and concomitant type II diabetes," *International Congress Series, Excerpta Medica*, Jan. 1, 1993, pp. 271-274.

Odawara, M., et al., "The Effect of Idebenone on Insulin Secretion in Elderly Diabetes Mellitus," *Age*, Jul. 1, 1995, vol. 18, No. 3, p. 140.

Sabbah, A., "Pharmacological, Biological and Clinical Effects of a New Anti-Asthmatic Fenspiride," *Pharmacologist*, Jan. 1, 1996, vol. 11, No. 2, p. 266.

Salem, H., et al., "Fenspiride—A Non-Sympathomimetic Bronchodilator with Anti-Allergic Activity," *Archives Internationales de Pharmacodynamie et de Therapie*, Sep. 1, 1971, vol. 193, No. 1, pp. 111-123.

Seitz, R.J., et al., "Stiff-person syndrome with anti-glutamic acid decarboxylase autoantibodies: complete remission of symptoms after intrathecal baclofen administration," *Journal of Neurology*, Oct. 1, 1995, vol. 242, No. 10, pp. 618-622.

Støa-Birketvedt, G., et al., "Cimetidine reduces weight and improves metabolic control in overweight patients with Type 2 diabetes," *International Journal of Obesity*, Nov. 1, 1998, vol. 22, pp. 1041-1045.

The Medical Letter on Drugs and Therapeutics, "Metformin/Rapaglinide (*PrandiMet*) for Type 2 Diabetes," Jun. 1, 2009, vol. 51, No. 1313, pp. 41-43.

Walker, B.R., et al., "Hyperkalemia after triamterene in diabetic patients," *Clinical Pharmacology and Therapeutics*, Jan. 1, 1972, vol. 13, No. 5, Part 1, pp. 643-651.

Weichenhain, B., et al., "Hypertension and Insulin Resistance: Glycaemia and Insulinaemia in Overweight Hypertensive Patients," *Drugs*, Jan. 1, 1993, vol. 46, Suppl. 2, pp. 183-188.

Yamashita, Y., et al., "Effect of 2-(4-Benzyl-Piperidino)-1-(4-Hydroxyphenyl)-1-Propanol on Blood Glucose Concentration," *Biochemical Pharmacology*, Dec. 15, 1979, vol. 28, pp. 3503-3506.

Yamashita, Y., et al., "General Pharmacological Activities of N-(2-methyl-3-chlorophenyl)-Anthranilic Acid (GEA 6414)," *Journal of the Medical Society of Toho University*, Jan. 1, 1981, vol. 28, No. 4, pp. 685-697.

Abedulla Khan, K., et al. "Pharmacodynamic drug interaction of mexiletine with metformin in rats" *Research Journal of Pharmaceutical, Biological and Chemical Sciences*, Jul. 1, 2012, pp. 905-911, vol. 3, No. 3.

Written Opinion in International Application No. PCT/EP2014/073201, dated Jan. 23, 2015, pp. 1-8.

Franco, F. et al. "Levosimendan is beneficial in diabetics with acute heart failure" *European Heart Journal*, Mar. 1, 2003, vol. 24, No. 5, abstract P2165, p. 407.

Foucquier, J. et al. "Analysis of drug combinations: current methodological landscape" *Pharmacology Research & Perspectives*, 2015, pp. 1-11, vol. 3, Issue 3, e00149.

Slinker, B. K. "The Statistics of Synergism" *J Mol Cell Cardiol*, 1998, pp. 723-731, vol. 30.

\* cited by examiner

COMPOSITIONS, METHODS AND USES FOR THE TREATMENT OF DIABETES AND RELATED CONDITIONS BY CONTROLLING BLOOD GLUCOSE LEVEL

CROSS-REFERENCE TO RELATED APPLICATION

This application is a continuation-in-part of International Patent Application No. PCT/EP2014/073201, filed Oct. 29, 2014.

FIELD OF THE INVENTION

The present invention relates to compositions and methods for controlling glycaemia in a mammalian in need thereof. More specifically, the present invention relates to novel therapies or combinatorial therapies of diabetes and related disorders, based on compositions controlling the blood glucose level.

BACKGROUND OF THE INVENTION

Diabetes mellitus refers to a group of metabolic diseases in which patients have high blood sugar level. It is a major public health problem due to high number of affected patients since 171 million people worldwide corresponding to 2.8% of the population in 2000 are diabetic. Diabetes is now considered as epidemic: the number of patients should almost double by 2030. There are mainly two types of diabetes. Type 1 diabetes is mainly characterized by insulin dependent patients, is known to be autoimmune, sometimes triggered by infection factors. It usually starts in patients younger than 30 and it accounts about 5-10% of all cases of diabetes [1]. Type 2 diabetes, mainly characterized by insulin independence, has a later onset than type 1 diabetes and is therefore named adult-onset diabetes. It accounts for about 90-95% of all diabetes cases. Many factors can potentially give rise to, or exacerbate type 2 diabetes. These include hypertension, elevated cholesterol, metabolic syndrome and overweight/obesity. As an example, approximately 90% of patients with type 2 diabetes are overweight/obese [2]. Other forms of diabetes include gestational diabetes, congenital diabetes, cystic fibrosis-related diabetes, steroid diabetes, and several forms of monogenic diabetes. Current treatments consist of insulin administration for type 1 diabetes and/or glucose-lowering medications or insulin sensitizers for type 2 diabetes. Insulin is a hormone involved in the glucose homeostasis, together with glucagon. In response to rising levels of blood glucose, insulin is produced by pancreatic beta cells located in the islets of Langerhans. Thus, glucose is taken up from the blood by hepatocytes, muscle cells, and adipocytes used either as energy source or for storage as glycogen and triglycerides. It also inhibits lipolysis, preventing fatty acid release from fat tissues. On the contrary, low blood glucose levels result both in a reduced production and release of insulin. Together with glucagon action, it results in glucose release into blood stream. In pathological situations, either insulin production by beta-cells is not sufficient (type 1 diabetes) and/or cells poorly respond to it (insulin resistance; type 2 diabetes), leading to persistent high levels of blood glucose. Precise mechanisms involved in these pathologies are not yet completely understood.

Decrease in insulin production characterizing type 1 diabetes is due to a destruction of beta-cells by an autoimmune process that consists of autoantibodies production, activation of self-reactive lymphocytes and infiltration of pancreas to destroy beta-cells. Type 2 diabetes mellitus is considered as a complex metabolic disorder. It results from the combination of impaired pancreatic insulin secretion due to beta-cells dysfunction, insulin resistance as well as damaged glucagon secretion. Impairment of glucose-stimulated production of insulin involves progressive loss of pancreatic beta-cells as well as a decline in islet cells function. Insulin resistance consists, for example, of suppressed or reduced effects of insulin in peripheral organs/tissues (liver, muscles and fat tissues) or enhanced lipolysis in adipocytes leading to increased circulation of free fatty acids. Those events result in increased endogenous glucose production by the liver together with decreased glucose uptake due to reduced insulin receptor expression, defects in post-receptor actions of insulin [3], hepatic glucose overproduction or blocking of insulin-signaling pathways [4]. Insulin resistance is a hallmark of a more complex syndrome, named metabolic syndrome that is a grouping of risk factors for coronary heart disease and diabetes mellitus including abdominal obesity, elevated triglyceride levels, decreased high-density lipoprotein levels, elevated blood pressure, and elevated fasting plasma glucose levels [5]. 75% of type 2 diabetes patients have metabolic syndrome.

Persistent high blood glucose leads both to acute and chronic complications that may be very disabling, even fatal for diabetic patients such as heart disease and stroke that are the most life-threatening consequences of diabetes mellitus. Long-term persistent elevated blood glucose damages blood vessels, leading to microvascular and macrovascular angiopathy which account for most of the increased morbidity and mortality associated with the disease. Microvascular complications are responsible for diabetic cardiomyopathy, nephropathy both sometimes leading to organ failure, retinopathy which can lead to severe vision loss and neuropathy. Macrovascular complications rather concern cardiovascular impairments that are responsible for coronary artery disease that in the end provokes angina or myocardial infarction, diabetic myonecrosis, peripheral vascular disease and stroke. Macrovascular complications are more common and up to 80% of patients with type 2 diabetes will develop or die of a macrovascular disease.

Unfortunately, existing treatments do not succeed in restoring normoglycaemia in the long term, since beta-cell function declines over time [6]. Moreover, there is presently no single drug able to reverse all aspects of the disease.

Control of glycaemia in type 1 diabetes is almost exclusively achieved with injections of exogenous insulin, since patients no longer produce insulin. Insulin may also be administered in type 2 diabetes patients, when glucose-lowering drugs and diet fail to control glycaemia [7]. It is nowadays more frequently administered to these patients, since it delays development and progression of complications. Use of insulin, however, comprises side effects including hypoglycaemia when dosage is not appropriate, increased risk of developing colorectal cancer [8] and gaining weight, which is not recommended for diabetic patients, particularly obese ones.

The progressive nature of type 2 diabetes implies that many patients will eventually require a combination of antidiabetics, possibly together with insulin [9]. Antidiabetics have been developed in order to counteract the main mechanisms involved in type 2 diabetes: insulin resistance (biguanides and thiazolidinediones) and insulin secretion (sulfonylureas, glinides, dipeptidylpeptidase-4 inhibitors, glucagon-like peptide 1 receptor agonists), in addition to particular mechanisms dealing with delayed absorption of glucose by gastrointestinal tract. However, most of these medications have been shown to have deleterious side effects such as weight gain, peripheral edema or congestive heart failure and to loss in efficiency in a long term use [9].

Despite the increasing number of therapeutic options related to diabetes, none is able to reverse all the aspects of the disease including progressive loss of beta cells function and the management of all the complications. Thus, there is a need for alternative and improved medications for the treatment of diabetes and related conditions.

SUMMARY OF INVENTION

The present invention provides novel compositions and methods for treating diabetes and related disorders, particularly type-2 diabetes.

The present invention also provides compositions and methods to normalize glycaemia in a mammalian subject in need thereof.

The invention also relates to compositions and methods for controlling blood glucose level in mammalian subjects, particularly in mammalian subjects having diabetes or a related disorder.

The invention also relates to compositions and methods for increasing or stimulating glucose uptake in adipocytes and/or muscular cells in mammalian subjects, particularly in mammalian subjects having diabetes or a related disorder.

The invention also relates to compositions and methods for decreasing insulin resistance in mammalian subjects having type-2 diabetes or a related disorder.

The invention also relates to compositions and methods for decreasing apoptosis of pancreatic beta cells in mammalian subjects, particularly in mammalian subjects having diabetes or a related disorder.

The present invention discloses the identification and validation, by the inventors, of drugs which, alone or in combination(s), do effectively affect either one or several relevant pathways involved in the control of blood glucose level and represent new and effective therapies for the treatment of diabetes and related disorders. The invention therefore discloses novel therapies of diabetes (type 1 or type 2) and related conditions, as well as novel drugs and drug combinations that are particularly effective for such conditions. The invention is applicable to any mammalian, particularly human subject. The invention is particularly suited for treating type-2 diabetes or metabolic syndrome, which are associated to abnormally elevated glucose blood levels. Treatments according to the invention may be used in combination or in alternation with other therapies of such conditions.

An object of the invention relates more specifically to a composition comprising at least one, preferably at least two compound(s) selected from acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine, for use in the treatment of diabetes or a related disorder.

In a preferred embodiment, said at least one, preferably at least two compound(s) is(are) selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide, or triamterene.

In another particular embodiment, the compound(s) is (are) selected from almitrine, azelastine, acamprosate, baclofen, carbetapentane, dexbrompheniramine, diethylcarbamazine, D-mannose, ifenprodil, mexiletine, nicergoline, or tolperisone.

As illustrated in the examples, the above compounds provide substantial effect when used individually and are further particularly effective in combinations. The examples indeed show that combinatorial therapies are even more preferred to regulate blood glucose levels, in particular glucose uptake and glucose production, as well as to decrease insulin resistance, and provide the most efficient clinical benefit.

Accordingly, a further object of this invention relates to a composition comprising at least:
  a first compound selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, and
  a second compound, distinct from the first compound, the second compound being selected from acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine, as well as to the use of such a composition in the treatment of diabetes or a related disorder.

Another object of the invention relates to a composition comprising at least two compounds selected from acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine, as well as to the use of such compositions in the treatment of diabetes or a related disorder in a mammalian in need thereof.

The at least two compounds are more preferably selected from selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene.

Drug compositions of this invention may also be used in further combination with other anti-diabetic agents or treatments in order provide improved clinical effect and/or to alleviate potential side effects of such anti-diabetic drugs or treatments.

Consequently, a further object of this invention relates to compositions comprising:
  a compound selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene; and
  a compound selected from the group consisting of acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, gemigliptin, glibenclamide, glibornuride, glicetanile, gliclazide, glimepiride, glipizide, gliquidone, glisentide, glycopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose;

as well as to the use of such compositions in the treatment of diabetes or a related disorder in a mammalian in need thereof.

An even more preferred object of this invention relates to compositions comprising a compound selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, in combination with metformin as well as to the use of such compositions in the treatment of diabetes or a related disorder in mammalian subject in need thereof.

An even more preferred object of this invention relates to compositions comprising a compound selected from the group consisting of torasemide, triamterene, baclofen or tolfenamic acid or salt(s) or sustained release formulation(s) thereof, in combination with metformin or a salt or sustained release formulation thereof.

The invention also relates to pharmaceutical compositions comprising a drug combination as disclosed above. The pharmaceutical compositions of the invention typically comprise one or several pharmaceutically acceptable excipients or carriers. Also, the compounds in the compositions of the invention may be used as such or in the form of a salt, hydrate, ester, ether, acid, amide, racemate, or isomer. They may also be in the form of sustained-release formulations. Prodrugs or metabolites of the compounds may be used as well.

In an embodiment the invention relates to a composition comprising a combination selected from:
ifenprodil and acamprosate,
ifenprodil and baclofen,
baclofen and acamprosate,
mexiletine and cinacalcet,
mexiletine and torasemide,
sulfisoxazole and torasemide,
azelastine and nicergoline,
idebenone and nicergoline,
carbetapentane and nicergoline,
almitrine and nicergoline,
cimetidine and nicergoline,
diethylcarbamazine and nicergoline,
ifenprodil and nicergoline,
azelastine and idebenone,
acamprosate and nicergoline,
azelastine and carbetapentane,
azelastine and almitrine,
idebenone and carbetapentane,
idebenone and almitrine,
triamterene and nicergoline,
D-Mannose and nicergoline,
idebenone and diethylcarbamazine,
ifenprodil and fenspiride,
ifenprodil and tolfenamic acid,
ifenprodil and torasemide,
ifenprodil and triamterene,
fenspiride and torasemide,
fenspiride and triamterene,
fenspiride and tolfenamic acid,
torasemide and tolfenamic acid,
torasemide and triamterene,
tolfenamic acid and triamterene, or
D-mannose and baclofen;

as well as to the use of such composition in the treatment of diabetes or a related disorder in a mammalian in need thereof.

In another embodiment the invention relates to a combination of metformin with at least one of the above combination of compounds, as well as its use in the treatment of diabetes or a related disorder in a mammalian in need thereof.

As will be further disclosed in the present application, the compounds in a composition or combinatorial therapy according to the invention may be formulated or administered to the subject together, separately or sequentially, possibly through different routes and protocols. In a preferred embodiment, compositions of the invention are administered repeatedly to the subject.

The invention also relates to methods of treating diabetes or a related disorder, the methods comprising administering to a subject in need thereof a drug or drug(s) composition as disclosed above. In a particular embodiment, the methods further comprise a step of measuring glucose blood level in a blood sample from the mammalian subject, either before or after drug(s) administration.

A further object of this invention relates to a method of treating diabetes or a related disorder, the method comprising simultaneously, separately or sequentially administering to a subject in need thereof a drug combination as disclosed above.

A further object of this invention relates to the use of the above described compositions for the manufacture of a medicament for the treatment of diabetes or a related disorder.

The invention may be used in any mammalian subject, particularly human subject.

BRIEF DESCRIPTION OF THE FIGURES

For all figures, tested drugs induce an effect significantly different from reference (t-test. *$p<0.05$. $p<0.01$; *$p<0.001$).

DETAILED DESCRIPTION OF THE INVENTION

Figure 1:
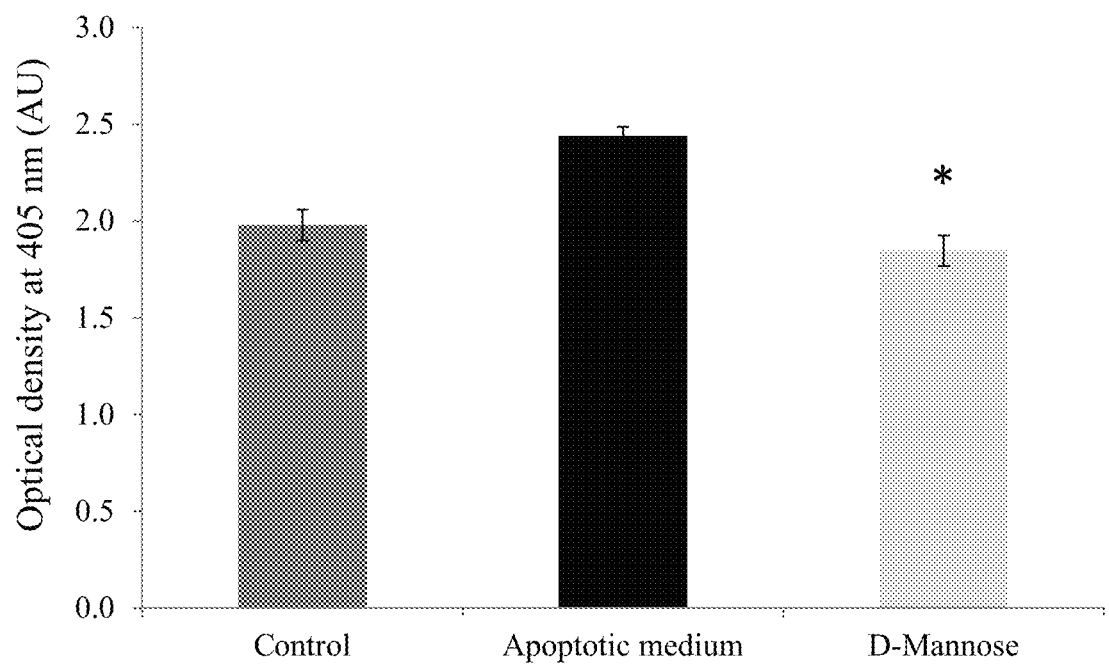
FIG. 1: Effect of D-mannose pre-treatment against apoptosis of beta cells (optical density). The apoptosis is significantly prevented by D-mannose at doses as low as 10 nM (129%).

The present invention provides new therapeutic approaches for controlling blood glucose level. The invention discloses novel drugs, drug combinations and methods, which allow an effective control of blood glucose level and may be used for patient treatment.

The invention therefore relates to compositions and methods for the treatment of diabetes and related disorders.

Definitions

Within the context of the invention, the term "treatment" includes the preventive or curative treatment. The term treatment designates in particular the correction, retardation, or reduction of an impaired glucose homeostasis. The level of glucose in blood fluctuates throughout the day. Glucose levels are usually lower in the morning, before the first meal of the day and rise after meals for some hours. Consequently, the term treatment includes the control of blood glucose level by increasing or decreasing blood glucose level depending on the condition of the mammalian subject and the day time in order to reach normal glucose levels. The term treatment more particularly includes a temporary or persistent reduction of blood glucose level in a subject having diabetes or a related disorder. The term "treatment" also designates an improvement in insulin release (e.g., by pancreatic β cells), glucagon release (e.g., by pancreatic α-cells), glucose utilization and/or uptake (e.g., capture of glucose by muscle cells or adipocytes), and/or hepatic neoglucogenesis.

Within the context of the invention, the terms "controlling the blood glucose level" or "the control of blood glucose level" refer to the normalization or the regulation of the blood or plasma glucose level in a mammalian subject having abnormal levels (i.e., levels that are below or above a known reference, median, or average value for a corresponding mammalian subject with a normal glucose homeostasis).

The term "diabetes" refers herein to a group of metabolic diseases in which patients have high blood glucose levels, including Type 1 diabetes, Type 2 diabetes, gestational diabetes, congenital diabetes, cystic fibrosis-related diabetes, steroid diabetes, and several forms of monogenic diabetes.

The term "related disorder" designates any disease associated with a blood or plasma glucose level outside the normal range, preferably hyperglycaemia. Consequently, the term "related disorder" includes impaired glucose tolerance (IGT), impaired fasting glucose (IFG), insulin resistance, metabolic syndrome, postprandial hyperglycaemia and overweight/obesity. Such related disorders can also be characterized by an abnormal blood and/or plasma insulin level.

The terms "combination" or "combinatorial therapy" or "combinatory treatment" designate a treatment wherein at least two compounds are co-administered to a subject to cause a biological effect. In a combined therapy according to this invention, the at least two drugs may be administered together or separately, at the same time or sequentially. Simultaneous administration is not required, as long as the drugs produce a combined or synergistic effect in the organism to improve the patient conditions. Also, the at least two drugs may be administered through different routes and protocols. As a result, although they may be formulated together, the drugs of a combination may also be formulated separately.

Within the context of the invention, the terms "compound" or "drug" as identified by its name or CAS number are meant to designate the chemical compound as specifically named or identified with its corresponding CAS number, as well as any pharmaceutically acceptable salt, hydrate, isomer, racemate, conjugate or derivative thereof, of any chemical purity.

The term "derivative" includes any functionally and structurally related compound, such as acid derivatives, amide derivatives, ester derivatives, ether derivatives, prodrugs and metabolites.

The term "prodrug" as used herein refers to any derivative (or precursor) of a compound which, when administered to a biological system (e.g., a human organism), generates said compound as a result of e.g., spontaneous chemical reaction(s), enzyme catalyzed chemical reaction(s), and/or metabolic chemical reaction(s). Prodrugs typically have the structure X-drug wherein X is an inert carrier moiety and drug is the active compound. Usually, the prodrug is devoid of activity or less active than the drug and the drug is released from the carrier in vivo. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [11-15]. Furthermore, the preparation of prodrugs may be performed by conventional methods known by those skilled in the art. Methods which can be used to synthesize prodrugs are described in numerous reviews on the subject [12; 16-21].

The term "metabolite" of a drug as used herein refers to a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug.

The term "salt" refers to a pharmaceutically acceptable and relatively non-toxic, inorganic or organic acid or basic addition salt of a compound of the present invention. Pharmaceutical salt formation typically consists of pairing an acidic, basic or zwitterionic drug molecule with a counterion to create a salt version of the drug. A wide variety of chemical species can be used in neutralization reaction. Though most of salts of a given active principle are bioequivalents, some may have, among others, increased solubility or bioavailability properties. Salt selection is now a common standard operation in the process of drug development as taught by H. Stahl and C. G Wermuth in their handbook [22].

In a preferred embodiment, the designation of a compound is meant to designate the compound per se, as well as any pharmaceutically acceptable salt, hydrate, isomer, racemate, ester or ether thereof.

In a more preferred embodiment, the designation of a compound is meant to designate the compound as specifically designated per se, as well as any pharmaceutically acceptable salt thereof.

In a particular embodiment, a sustained-release formulation of the compound is used.

Compositions and Methods for Treating Diabetes and Related Disorders

By a comprehensive integration of experimental data covering results of cell biology studies, expression profiling experiments and genetic association studies, the inventors have been able to select a small number of drugs which, alone and/or in combination(s), effectively alter relevant pathways for the control of glycaemia and represent new therapeutic approaches for treating diabetes and related disorders. These drugs or combinations may be used to normalise blood glucose level by acting e.g., on insulin release, glucagon release, glucose utilization and/or glucose production, and offer novel potent therapies of diabetes and related disorders. As disclosed in the examples, these drugs and combinations have a strong effect on diabetes' relevant functions: they are involved in the protection of beta cells against apoptosis, the increase of glucose uptake in muscular tissues and in adipocytes, the increase of insulin secretion by the pancreatic β cells and/or in the control of glucose production in hepatic tissues.

These drugs and combinations therefore represent new therapeutic approaches for the control of blood glucose level in a mammalian in need thereof. They also represent new therapeutic approaches for the treatment of diabetes or related disorders in a mammalian in need thereof.

In this regard, an object of this invention relates to compositions comprising at least one compound selected from the group consisting of acamprosate, amlexanox, almitrine, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone and rilmenidine, for use in the treatment of diabetes or a related disorder in a mammalian in need thereof.

The invention also relates to the use of at least one compound as listed above for the manufacture of a medicament for treating diabetes or a related disorder in a mammalian in need thereof.

The invention also relates to a method for treating diabetes or a related disorder in a mammalian in need thereof, comprising administering to the mammalian at least one compound as listed above.

Illustrative CAS numbers for each of the selected compounds are provided in Table 1 below:

TABLE 1

| Drug Name | CAS number |
| --- | --- |
| acamprosate | 77337-76-9; 77337-73-6 |
| almitrine | 27469-53-0; 29608-49-9 |
| amlexanox | 68302-57-8; |
| azelastine | 58581-89-8; 79307-93-0 |
| baclofen | 1134-47-0; 66514-99-6; 69308-37-8; 70206-22-3; 63701-56-4; 63701-55-3 |
| carbetapentane | 77-23-6; 23142-01-0; 1045-21-2 |
| cimetidine | 51481-61-9; 70059-30-2 |

TABLE 1-continued

| Drug Name | CAS number |
| --- | --- |
| cinacalcet | 226256-56-0; 364782-34-3 |
| dexbrompheniramine | 86-22-6; 980-71-2; 2391-03-9 |
| diethylcarbamazine | 90-89-1; 1642-54-2 |
| diprophylline | 479-18-5 |
| D-mannose | 10030-80-5; 3458-28-4 |
| fenspiride | 5053-06-5; 5053-08-7 |
| fexofenadine | 83799-24-0; 138452-21-8; 153439-40-8; 139965-10-9; 139965-11-0 |
| idebenone | 58186-27-9 |
| ifenprodil | 23210-56-2; 23210-58-4 |
| levosimendan | 141505-33-1 |
| mexiletine | 5370-01-4; 31828-71-4 |
| nicergoline | 27848-84-6 |
| piribedil | 3605-01-4 |
| rilmenidine | 54187-04-1; 85409-38-7 |
| tolfenamic acid | 13710-19-5 |
| tolperisone | 728-88-1; 3644-61-9 |
| torasemide | 56211-40-6; 72810-59-4 |
| triamterene | 396-01-0 |

As mentioned in the examples, the above compounds, when tested individually, are active to improve glucose levels by altering distinct important pathways of glucose homeostasis.

Furthermore, the inventors have surprisingly found that acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide and triamterene, are particularly efficient in protecting beta cells against apoptosis, in improving the glucose uptake by muscular tissues and/or the release of insulin. Such compounds therefore represent the most preferred embodiment for use in the present invention.

Consequently, the compositions of the invention may comprise 1, 2, 3, 4 or 5 distinct above drugs, more preferably 2, 3 or 4 distinct drugs for combinatorial treatment of diabetes or a related disorder in a subject in need thereof. Furthermore, the above drug compositions may also be used in further combination with one or several additional drugs or treatments beneficial to subjects suffering from diabetes or a related disorder.

In this regard, a particular object of the invention relates to a composition for use in the treatment of diabetes or a related disorder, the composition comprising a compound selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene.

The above molecules are used preferably, in combination therapies to provide the most efficient clinical benefit. Drug combinations are particularly advantageous because they can affect different pathways and thus are more effective. Also, because of their efficacy and mode of action, the drug combinations can be used at low dosages, which is a further very substantial advantage. Thus, most preferred drug compositions comprise 2, 3, 4 or 5 distinct drugs, even more preferably 2, 3 or 4 for combinatorial treatment of diabetes or a related disorder in a subject in need thereof. In a preferred embodiment, the drugs of the invention are used in combination(s) for combined, separate or sequential administration, in order to provide the most effective effect.

In this regard, a preferred object of this invention relates to compositions comprising a combination of at least two compounds chosen from the group consisting of acamprosate, almitrine, amlexanox, azelastine, baclofen, carbetapentane, cinacalcet, dexbromopheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone and rilmenidine, as well as to the use of such compositions in the treatment of diabetes or a related disorder in a mammalian in need thereof.

A more preferred object of this invention relates to compositions comprising a combination of at least two compounds selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide and triamterene, as well as to the use of such compositions the treatment of diabetes or a related disorder in a mammalian in need thereof.

A further object of this invention relates to a composition comprising:
  at least one compound selected from acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, and
  at least one distinct compound being selected from acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine,
as well as to the use of such a composition in the treatment of diabetes or a related disorder.

Another object of this invention relates to compositions comprising (i) ifenprodil and (ii) a compound selected from the group consisting of acamprosate, almitrine, amlexanox, azelastine, baclofen, carbetapentane, cinacalcet, dexbrompheniramine, diethylcarbamazine, D-Mannose, fenspiride, fexofenadine, mexiletine, nicergoline, tolperisone, torasemide, triamterene, tolfenamic acid, piribedil, levosimendan, cimetidine, diprophylline, idebenone or rilmenidine, as well as to the use of such composition in the treatment of diabetes or a related disorder in a mammalian in need thereof.

A further object of this invention relates to compositions comprising (i) acamprosate and (ii) a compound selected from the group consisting of almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine, as well as to the use of such composition in the treatment of diabetes or a related disorder in a mammalian in need thereof.

A particular object of this invention relates to compositions comprising (i) azelastine and (ii) a compound selected from the group consisting of acamprosate, almitrine, amlexanox, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone or rilmenidine, as well as to the use of such composition in the treatment of diabetes or a related disorder in a mammalian in need thereof.

Another particular object of this invention relates to compositions comprising (i) torasemide and (ii) a compound selected from the group consisting of acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, triamterene, tolfenamic acid, piribedil, levosimendan, cimetidine, diprophylline, idebenone or rilmenidine, as well as to the use of such composition in the treatment of diabetes or a related disorder in a mammalian in need thereof.

An object of this invention relates to compositions comprising (i) fenspiride and (ii) a compound selected from the group consisting of acamprosate, almitrine, amlexanox, azelastine, baclofen, carbetapentane, cinacalcet, dexbrompheniramine, diethylcarbamazine, D-mannose, fexofenadine, ifenprodil, mexiletine, nicergoline, tolperisone, torasemide, triamterene, tolfenamic acid, piribedil, levosimendan, cimetidine, diprophylline, idebenone or rilmenidine, as well as to the use of such composition in the treatment of diabetes or a related disorder in a mammalian in need thereof.

A particular object of this invention relates to compositions comprising (i) tolfenamic acid and (ii) a compound selected from the group consisting of acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, piribedil, levosimendan, cimetidine, diprophylline, idebenone or rilmenidine, as well as to the use of such composition in the treatment of diabetes or a related disorder in a mammalian in need thereof.

A particular object of this invention relates to compositions comprising (i) triamterene and (ii) a compound selected from the group consisting of acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, tolfenamic acid, piribedil, levosimendan, cimetidine, diprophylline, idebenone or rilmenidine, as well as to the use of such composition in the treatment of diabetes or a related disorder in a mammalian in need thereof.

Another particular object of this invention relates to compositions comprising (i) piribedil, and (ii) a compound selected from the group consisting of acamprosate, almitrine, amlexanox, azelastine, baclofen, carbetapentane, cinacalcet, dexbrompheniramine, diethylcarbamazine, D-mannose, fenspiride, fexofenadine, ifenprodil, mexiletine, nicergoline, tolperisone, torasemide, triamterene, tolfenamic acid, levosimendan, cimetidine, diprophylline, idebenone or rilmenidine, as well as to the use of such composition in the treatment of diabetes or a related disorder in a mammalian in need thereof.

In a most preferred embodiment, the compositions of this invention comprise at least one of the following drug combinations, for combined, separate or sequential administration:
  ifenprodil and acamprosate,
  ifenprodil and baclofen,
  baclofen and acamprosate,
  mexiletine and cinacalcet,
  mexiletine and torasemide, sulfisoxazole and torasemide,
azelastine and nicergoline,
idebenone and nicergoline,
carbetapentane and nicergoline,
almitrine and nicergoline,
cimetidine and nicergoline,
diethylcarbamazine and nicergoline,
ifenprodil and nicergoline,
azelastine and idebenone,
acamprosate and nicergoline,
azelastine and carbetapentane,
azelastine and almitrine,
idebenone and carbetapentane,
idebenone and almitrine,
triamterene and nicergoline,
D-Mannose and nicergoline,
idebenone and diethylcarbamazine,
ifenprodil and fenspiride,
ifenprodil and torasemide,
ifenprodil and triamterene,
ifenprodil and tolfenamic acid,
fenspiride and torasemide,
fenspiride and triamterene,
fenspiride and tolfenamic acid,
torasemide and triamterene,
torasemide and tolfenamic acid,
triamterene and tolfenamic acid, or
D-mannose and baclofen.

Another object of this invention resides in the use of a composition as defined above for controlling blood or plasma glucose level in a mammalian in need thereof.

A further object of this invention resides in the use of a composition as defined above for the manufacture of a medicament for controlling blood or plasma glucose level in a mammalian in need thereof.

A further object of this invention resides in the use of a composition as defined above for the manufacture of a medicament for treating diabetes or a related disorder.

As indicated previously, in a composition or combination therapy of this invention, the compounds or drugs may be formulated together or separately, and administered together, separately or sequentially.

The invention is particularly adapted for correcting dysregulations of glucose levels in human patients having diabetes, pre-diabetes (also referred to as IGT or IFG), metabolic syndrome, obesity, or a cardiovascular disease implying a predisposition to diabetes.

A further object of the invention is a method of treating diabetes or a related disorder, the method comprising simultaneously, separately or sequentially administering to a subject in need thereof an effective amount of a drug or drug combination as defined above.

In a preferred embodiment, the invention relates to a method of treating diabetes or a related disorder in a subject in need thereof, comprising administering simultaneously, separately or sequentially to the subject an effective amount of at least one of the following drug combinations:
ifenprodil and acamprosate,
ifenprodil and baclofen,
baclofen and acamprosate,
mexiletine and cinacalcet,
mexiletine and torasemide,
sulfisoxazole and torasemide,
azelastine and nicergoline,
idebenone and nicergoline,
carbetapentane and nicergoline,
almitrine and nicergoline,
cimetidine and nicergoline,
diethylcarbamazine and nicergoline,
ifenprodil and nicergoline,
azelastine and idebenone,
acamprosate and nicergoline,
azelastine and carbetapentane,
azelastine and almitrine,
idebenone and carbetapentane,
idebenone and almitrine,
triamterene and nicergoline,
D-Mannose and nicergoline,
idebenone and diethylcarbamazine,
ifenprodil and fenspiride,
ifenprodil and torasemide,
ifenprodil and triamterene,
ifenprodil and tolfenamic acid,
fenspiride and torasemide,
fenspiride and triamterene,
fenspiride and tolfenamic acid,
torasemide and triamterene,
torasemide and tolfenamic acid,
triamterene and tolfenamic acid, or
D-mannose and baclofen.

In a particular embodiment, the methods of treating diabetes or a related disorder further comprise a step of measuring glucose blood level in a blood sample from the mammalian subject, either prior to and/or after administration of the drug(s).

In this regard, a further object of the invention is a method of controlling blood glucose level, the method comprising the steps of:

1) measuring blood glucose level in a blood sample from a mammalian subject, 2) administering to said subject an effective amount of a composition as disclosed above.

In the methods of the invention, the step of measuring glucose level may be repeated during the course of the treatment, e.g., to assess or monitor treatment efficacy and/or to adjust treatment regimen.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

According to preferred embodiments of the invention, as indicated above, the compounds are used as such or in the form of a pharmaceutically acceptable salt, prodrug, metabolite, or sustained release formulation thereof.

Although very effective in vitro and in vivo, depending on the subject or specific condition, the above methods, compositions or combination therapies may further be used in conjunction or association or combination with additional drugs or treatments.

Other additional diabetes therapies used in conjunction with drug(s) or drug(s) combination(s) according to the present invention, may comprise one or more drug(s) that regulate blood glucose level, one or more drug(s) used for the treatment of hyperlipidaemia or hypercholesterolemia, one or more drug(s) that could be used, or currently evaluated in the frame of clinical trials, for treating diabetes or a related disorder. Preferably, said one or more drug(s) is/are selected from acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, gemigliptin, glibenclamide, glibornuride, glicetanile, gliclazide, glimepiride, glipizide, gliquidone, glisentide, glyclopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose.

Illustrative CAS numbers for each of these compounds are provided in Table 2 below (side effects mainly from Sweetman S (Ed), Martindale: The complete drug reference. London: Pharmaceutical Press. Electronic version, (Edition 2011) and Nathan et al. (2009) [9]):

TABLE 2

| Drug Name | CAS number | Side Effects |
|---|---|---|
| Analogs of amylin | | |
| pramlintide | 196078-30-5 | Gastrointestinal Weight loss |
| Glucagon-like peptide 1 receptor agonists | | |
| exenatide | 141758-74-9 | Gastrointestinal |
| liraglutide | 204656-20-2 | Weight loss |
| Alphaglucosidase inhibitors | | |
| acarbose | 56180-94-0 | Gastrointestinal |
| miglitol | 72432-03-2 | |
| voglibose | 83480-29-9 | |
| Dipeptidyl peptidase 4 inhibitors | | |
| alogliptin | 850649-62-6 | Upper respiratory infections |
| berberine | 2086-83-1; 633-65-8; 633-66-9 | |
| dutogliptin | 852329-66-9 | |
| gemigliptin | 911637-19-9 | |
| linagliptin | 668270-12-0 | |
| saxagliptin | 361442-04-8 | |
| sitagliptin | 654671-78-0 | |
| vildagliptin | 274901-16-5 | |
| Glinides | | |
| mitiglinide | 145375-43-5 | Weight gain |
| nateglinide | 105816-04-4 | Cardiovascular complications |
| repaglinide | 135062-02-1 | Hypoglycaemia |
| Sulfonylureas | | |
| acetohexamide | 968-81-0 | Weight gain |
| carbutamide | 339-43-5 | Cardiovascular complications |
| chlorpropamide | 94-20-2 | |
| glibenclamide | 10238-21-8 | Hypoglycaemia |
| glibornuride | 26944-48-9 | Loss of efficacy with long term use |
| glipizide | 29094-61-9 | |
| glimepiride | 93479-97-1 | |
| gliclazide | 21187-98-4 | |
| gliquidone | 33342-05-1 | |
| glisentide | 32797-92-5 | |
| glyclopyramide | 631-27-6 | |
| tolbutamide | 64-77-7 | |
| tolazamide | 1156-19-0 | |
| Fibrate | | |
| bezafibrate | 41859-67-0 | Gastrointestinal |
| ciprofibrate | 52214-84-3 | Myopathy |
| clofibrate | 637-07-0; 882-09-7; 39087-48-4; 14613-30-0 | |

TABLE 2-continued

| Drug Name | CAS number | Side Effects |
|---|---|---|
| fenofibrate | 49562-28-9 (fenofibrate); 42017-89-0 (fenofibric acid); 856676-23-8 | |
| gemfibrozil | 25812-30-0 | |
| Thiazolidinediones | | |
| rosiglitazone | 122320-73-4; 302543-62-0; 155141-29-0; 397263-60-4 | Peripheral oedema Congestive heart failure |
| pioglitazone | 111025-46-8; 112529-15-4 | |
| Biguanides | | |
| buformin | 1190-53-0 | Gastrointestinal |
| metformin | 657-24-9; 1115-70-4 | Lactic acidosis |
| phenformin | 834-28-6 | |
| Others | | |
| bromocriptine | 22260-51-1 | Gastrointestinal, hypotension, cardiovascular complications |
| chromium picolinate | 14639-25-9 | N/A |
| colesevelam | 182815-44-7 | Gastrointestinal Hyperchloraemic acidosis Increase of plasma-triglyceride concentrations |
| dexfenfluramine | 3239-44-9 | Cardiovascular complications |
| imidapril | 89396-94-1 | Hypotension Cardiovascular complications Renal impairment Upper respiratory tract symptoms Pancreatitis |
| inulin | 9005-80-5 | N/A |
| lipoic acid | 62-46-4 | N/A |
| mecobalamin | 13422-55-4 | N/A |
| orlistat | 96829-58-2 | Gastrointestinal Risk of liver toxicity |
| Insulin | | |
| insulin | 9004-10-8; 11070-73-8; 12584-58-6; 11061-68-0; 8063-29-4; 9004-21-1; 68859-20-1; 8049-62-5; 53027-39-7; 9004-17-5; 116094-23-6; 9004-12-0; 51798-72-2; 11091-62-6 169148-63-4; 160337-95-1; 207748-29-6; 133107-64-9; 874442-57-6 | Hypoglycaemia Weight gain |

In this regard, an object of this invention relates to compositions comprising:
  at least one compound selected from the group consisting of acamprosate, almitrine, amlexanox, azelastine, baclofen, carbetapentane, cinacalcet, dexbromopheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone and rilmenidine, and
  at least one compound, selected from the group consisting of acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, gemigliptin, glibenclamide, glibornuride, glicetanile, gliclazide, glimepiride, glipizide, gliquidone, glisentide, glyclopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose, as well as to the use of such compositions in the treatment of diabetes or a related disorder level in mammalian subject in need thereof.

Another preferred object of this invention relates to compositions comprising (i) a compound selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, triamterene or torasemide, in combination with (ii) a compound selected from the group consisting of acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, glibenclamide, glibornuride, glicetanile, gliclazide, glimepiride, glipizide, gliquidone, glisentide, glyclopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose, as well as to the use of such compositions in the treatment of diabetes or a related disorder in mammalian subject in need thereof.

An even more preferred object of this invention relates to compositions comprising a compound selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, in combination with one compound selected from the group consisting of glibenclamide, repaglinide, metformin and pioglitazone, as well as to the use of such compositions in the treatment of diabetes or a related disorder in mammalian subject in need thereof.

A very preferred object of this invention relates to compositions comprising a compound selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, in combination with metformin, as well as to the use of such compositions in the treatment of diabetes or a related disorder in mammalian subject in need thereof.

An even more preferred object of this invention relates to compositions comprising a compound selected from the group consisting of torasemide, triamterene, baclofen, tolfenamic acid or salt(s) or sustained release formulation(s) thereof, in combination with metformin or a salt or sustained release formulation thereof, as well as to the use of such compositions in the treatment of diabetes or a related disorder in mammalian subject in need thereof.

Another preferred object of this invention relates to compositions comprising one of the following combinations of compounds:
torasemide and metformin,
triamterene and metformin,
baclofen and metformin, or
tolfenamic acid and metformin
or salt(s) or sustained release formulation(s) thereof, as well as to the use of such compositions in the treatment of diabetes or a related disorder in mammalian subject in need thereof.

A more preferred object of this invention relates to compositions comprising (i) at least two compounds selected from the group consisting of acamprosate, almitrine, amlexanox, azelastine, baclofen, carbetapentane, cinacalcet, dexbromopheniramine, diethylcarbamazine, D-mannose, fenspiride, fexofenadine, ifenprodil, mexiletine, nicergoline, tolperisone, torasemide, triamterene, tolfenamic acid, piribedil, levosimendan, cimetidine, diprophylline, idebenone and rilmenidine, and a compound selected from the group consisting of acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, gemigliptin, glibenclamide, glibornuride, glicetanile, gliclazide, glimepiride, glipizide, gliquidone, glisentide, glyclopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose, as well as to the use of such compositions in the treatment of diabetes or a related disorder in mammalian subject in need thereof.

A more preferred object of this invention relates to compositions comprising:
at least two compounds selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene,
in combination with a compound selected from the group consisting of acarbose, acetohexamide, alogliptin, berberine, bezafibrate, bromocriptine, buformin, carbutamide, chlorpropamide, chromium picolinate, ciprofibrate, clofibrate, colesevelam, dexfenfluramine, dutogliptin, exenatide, fenofibrate, gemfibrozil, gemigliptin, glibenclamide, glibornuride, glicetanile, gliclazide, glimepiride, glipizide, gliquidone, glisentide, glyclopyramide, imidapril, insulin, inulin, lipoic acid, linagliptin, liraglutide, mecobalamin, metformin, miglitol, mitiglinide, nateglinide, orlistat, phenformin, pioglitazone, pramlintide, repaglinide, rosiglitazone, saxagliptin, sitagliptin, tolazamide, tolbutamide, vildagliptin and voglibose,
as well as to the use of such compositions in the treatment of diabetes or a related disorder in mammalian subject in need thereof.

An even more preferred object of this invention relates to compositions comprising at least two compounds selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, in combination with one compound selected from the group consisting of glibenclamide, repaglinide, metformin and pioglitazone, as well as to the use of such compositions in the treatment of diabetes or a related disorder in mammalian subject in need thereof. Another preferred object of this invention relates to compositions comprising at least two compounds selected from the group consisting of acamprosate, almitrine, azelastine, baclofen, carbetapentane, cinacalcet, dexbrompheniramine, diethylcarbamazine, D-mannose, fenspiride, ifenprodil, levosimendan, mexiletine, nicergoline, tolfenamic acid, tolperisone, torasemide or triamterene, in combination with one compound selected from the group consisting of bezafibrate, ciprofibrate, clofibrate, gemfibrozil, fenofibrate, orlistat, as well as to the use of such compositions in the treatment of diabetes or a related disorder in mammalian subject in need thereof.

Another preferred object of this invention relates to compositions comprising baclofen and acamprosate, in combination with one compound selected from the group consisting of pioglitazone, rosiglitazone, bezafibrate, ciprofibrate, clofibrate, fenofibrate, gemfibrozil, buformin, colesevelam, orlistat, as well as to the use of such compositions in the treatment of diabetes or a related disorder in mammalian subject in need thereof.

A more preferred object of this invention relates to compositions comprising metformin in combination with at least one of the following combination of compounds:
　　ifenprodil and acamprosate,
　　ifenprodil and baclofen,
　　baclofen and acamprosate,
　　mexiletine and cinacalcet,
　　mexiletine and torasemide,
　　sulfisoxazole and torasemide,
　　azelastine and nicergoline,
　　idebenone and nicergoline,
　　carbetapentane and nicergoline,
　　almitrine and nicergoline,
　　cimetidine and nicergoline,
　　diethylcarbamazine and nicergoline,
　　ifenprodil and nicergoline,
　　azelastine and idebenone,
　　acamprosate and nicergoline,
　　azelastine and carbetapentane,
　　azelastine and almitrine,
　　idebenone and carbetapentane,
　　idebenone and almitrine,
　　triamterene and nicergoline,
　　D-Mannose and nicergoline,
　　idebenone and diethylcarbamazine,
　　ifenprodil and fenspiride,
　　ifenprodil and torasemide,
　　ifenprodil and triamterene,
　　ifenprodil and tolfenamic acid,
　　fenspiride and torasemide,
　　fenspiride and triamterene,
　　fenspiride and tolfenamic acid,
　　torasemide and triamterene,
　　torasemide and tolfenamic acid,
　　triamterene and tolfenamic acid, or
　　D-mannose and baclofen.

Another more preferred object of this invention relates to the use of such compositions in the treatment of diabetes or a related disorder in mammalian subject in need thereof. The above combinations comprising one or more drugs of the invention and a known drug listed in Table 2, or a combination thereof, allow a diminution of the dosage of these drugs for the treatment of diabetes. This lowering permits to avoid or delay appearance of known drawbacks for these drugs (Table 2; e.g. resistance to treatment increasing with time, weight gain, peripheral oedema, renal toxicity due to lactic acidosis).

As already mentioned, in the above mentioned combinatorial therapies, drugs may be administered together or separately, at the same time or sequentially depending on the specific pharmacokinetic features of each drug in order to produce a combined or synergistic effect in the organism.

The above combinations can also be used in conjunction with any other therapy used for regulating glucose blood level; such therapy can be, more particularly, the well-known diabetes specific diet (high in dietary fiber, low in fat, low in sugar), natural supplement as extracts or part of *Cinnamonum cassia*, moringa, *ginseng*, gymnema, aloe vera, walnut leaf, myrcia, garlic, *Grifola frondosa, Reishi, Agaricus blazei, Agrocibe cylindracea, Cordyceps*, agrimony, alfalfa, coriander, eucalyptus, juniper, as well as oligo elements like chromium, vanadium, magnesium, or zinc.

Therapy according to the invention may be provided at home, the doctor's office, a clinic, a hospital's outpatient department, or a hospital, so that one can observe the therapy's effects closely and make any adjustments that are needed as a function of measured blood glucose level.

The duration of the therapy depends on the stage of the disease being treated, age and condition of the patient, and how the patient responds to the treatment. The dosage, frequency and mode of administration of drugs or each component of the drug combinations of the invention can be controlled independently. For example, one drug of a combination may be administered orally while the second drug may be administered intramuscularly or at different times through the day. The drugs may also be formulated together such that one administration delivers all drugs.

The treatment of the invention can be administered during particular periods of the day, for example, on time or just before or just after the time the glucose concentration reaches its peak in the plasma. Glycaemia can easily be determined, even by the patients themselves, using different commercially available glucometers. The time and dosage of the treatment can therefore be adapted as a function of the measured glycaemia. If there is sequential administration, the administration can be dependent on the blood glucose concentration for example the first active ingredient is administered before the glucose peak while the other is administered after the glucose peak. Usually, the glucose concentration reaches its peak in the plasma of a subject after meals.

The administration of each drug of the combination may be by any suitable means that results in a concentration of the drug that, combined with the other component, is able to control blood glucose levels.

While it is possible for the drug or the drugs of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the compositions of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug(s) within the body over an extended period of time; (ii) formulations that after a predetermined lag time create a substantially constant concentration of the drug(s) within the body over an extended period of time; (iii) formulations that sustain drug(s) action during a predetermined time period by maintaining a relatively, constant, effective drug level in the body with concomitant minimization of undesirable side effects associated with fluctuations in the plasma level of the active drug substance; (iv) formulations that localize drug(s) action by, e.g., spatial placement of a controlled release composition adjacent to or in the diseased tissue or organ; and (v) formulations that target drug(s) action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly-(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

Composition according to the invention is administered to a subject orally or by subcutaneous, intravenous or intramuscular injections, at different times of day, to alter the blood glucose level. In carrying out this process, where it is desired to modify, regulate, or normalize the blood glucose level of a mammalian, to treat diabetes or a related disorder, or both, composition of the invention is administered in dosage amount sufficient to alter, regulate or normalize the glucose level in the blood of the subject. Composition of the invention can be administered to a mammalian, particularly a human, exhibiting abnormal blood glucose level, in particular period of day, for example, on time or just before or just after the time the glucose concentration reaches its peak in the plasma. The level of glucose in the blood of mammalian is time-of-day dependent, and cyclic. Glucose level in blood is rising and falling at different times of day preferably dependent on the time of meals and physical activity/exercise. Usually, the glucose concentration reaches its peak in the plasma of a subject after meals, therefore composition of the invention can be, for example, preferably administered from 2 hours before meals to 2 hours after meals, more preferably from one hour before meals to one hour after meals and even more preferably during meals to achieve maximal therapeutic efficacy.

It will be appreciated that the drugs of the combination may be administered concomitantly, either in the same or different pharmaceutical formulation or sequentially. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for controlling blood or plasma glucose levels.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impaired glucose levels where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use suboptimal doses of each compound, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as 1/20, 1/30, 1/50, 1/100, or even lower, of therapeutic doses are used.

At such sub-therapeutic dosages, the compounds would exhibit no or less side effects, while the combinations according to the invention are fully effective in controlling glucose blood or plasma levels.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:

Acamprosate orally from about 9 to 200 mg per day,
Almitrine orally from about 0.5 to 10 mg per day,
Amlexanox orally from about 0.75 to 15 mg per day,
Azelastine orally from about 0.04 to 0.4 mg per day,
Baclofen orally from about 0.15 to 50 mg per day,
Carbetapentane orally from about 0.6 to 18 mg per day,
Cimetidine orally from about 4 to 160 mg per day,
Cinacalcet orally from about 0.3 to 36 mg per day,
D-mannose orally from 0.01 to 1.6 g per day,
Dexbrompheniramine orally from about 0.06 to 1.2 mg per day,
Diethylcarbamazine orally from about 0.6 to 600 mg per day,
Diprophylline orally from about 9 to 320 mg per day,
Fenspiride orally from 1.6 to 24 mg per day,
Fexofenadine orally from 1.2 to 18 mg per day,
Idebenone orally from about 4.5 mg to 225 mg per day,
Ifenprodil orally from about 0.4 to 6 mg per day,
Levosimendan orally from about 0.05 to 4 mg per day,
Metformin orally from about 1 mg to 2.5 mg per day,
Mexiletine orally from about 6 to 120 mg per day,
Nicergoline orally from about 0.6 to 6 mg per day,
Piribedil orally from about 0.8 to 25 mg per day,
Rilmenidine orally from about 10 to 200 µg per day,
Tolperisone orally from about 1.5 to 4.5 mg per day,
Tolfenamic acid orally from about 3 to 60 mg per day,
Torasemide orally from about 0.05 to 4 mg per day,
Triamterene orally from about 1.5 to 25 mg per day.

In combinations of the invention, the molar ratio between drugs may vary e.g., from 0.001 to 1000. Also, the ratio of the drug(s) and excipient in a composition of the invention advantageously vary between 0.001 and 1000.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

Diabetes is a metabolic disease that profoundly affects energy homeostasis and the high plasmatic level of glucose observed in patients can have multiple causes. Type 1 diabetes is characterized by the destruction of β cells of Langerhans islets. Type 2 diabetes is characterized, in part, by a decrease of the production of insulin by the pancreatic β cells, a progressive death of β cells, insulin resistance (i.e. lower capture of glucose by muscle cells and adipocytes), or an abnormal elevation of hepatic gluconeogenesis. Hence, the efficacy determination of candidate compounds is based on several in vitro and in vivo studies in order to address most of the metabolic and physiological impairments characterizing this complex pathology. The drugs were first tested individually, followed by assays of their combinatorial action. Drug activity is determined on various models which illustrate different physiological features representative of an abnormal blood glucose level such as those involved in diabetes or related disorders.

1. In Vitro Studies 1.1 Prevention of Beta Cells Apoptosis

Drugs of the invention have been tested for their efficiency in protecting beta cells from apoptosis. Such activity could be considered of use in type 1 diabetes as well as in type 2 diabetes.

Cell Culture and Media

The beta pancreatic INS-1 cells have been selected for this study. The cells are cultured in complete medium, RPMI 1640 10 mM glucose supplemented with 1 mM sodium pyruvate, 50 μM 2-mercaptoethanol, 2 mM glutamine, 10 mM HEPES, 100 IU/mL penicillin, 100 μg/mL streptomycin and 10% heat-inactivated foetal calf serum (FCS), as described by Asfari et al. (23). INS-1 cells are plated ($4.5 \times 10^4$ cells/well) in 96-well poly ornithine coated plates and cultured at 37° C. in a humidified atmosphere of 95% air/5% $CO_2$. The day after, cells are pre-incubated with the tested molecules for 1 h. Then, after a medium change, cells are cultured for 24 h in a medium containing the tested molecules and glucose 30 mM, myristic acid 0.05 mM, INF 25 ng/mL, TNF 25 ng/mL and IL 5 ng/mL.

Apoptosis Quantification

The efficacy of compounds to prevent apoptosis is then evaluated by the highly specific apoptosis detection kit from Chemicon (Ref. APT225). This procedure is based on the detection of single-stranded DNA (ssDNA) which is a specific marker of apoptotic cells (24).

Results are expressed in optical density (OD) arbitrary unit and % of reduction of the apoptosis induced by apoptotic condition. Following a Dunnett t-test, all compounds showing a significant decrease in % of apoptotic cells compared to apoptotic control condition are considered active.

Results

Results are shown in FIG. 1 and Table 3 and demonstrate that the drugs of the invention when tested alone, induce a substantial protective effect against apoptosis of beta cells. In FIG. 1, D-mannose induces a significant and complete protection of beta cells against apoptosis when compared to non-treated cell in apoptotic conditions. D-mannose confers more than 129% of protection against apoptosis. Similarly, Table 3 displays the percentage of protection conferred by drugs of the invention.

TABLE 3

| Drugs | Percentage of apoptosis reduction |
| --- | --- |
| D-mannose | 129% |
| Mexiletine | 74% |
| Tolperisone | 78% |
| Baclofen | 84% |
| Cinacalcet | 167% |
| Dexbrompheniramine | 76% |
| Diethylcarbamazine | 44% |
| Nicergoline | 112% |
| Torasemide | 67% |
| Triamterene | 64% |
| Almitrine | 103% |
| Azelastine | 81% |
| Acamprosate | 49% |
| Carbetapentane | 103% |
| Ifenprodil | 54% |
| Levosimendan | 118% |

1.2 Insulin Secretion in Response to Glucose Stimulation

Cell Culture and Media

The beta pancreatic INS-1 cells have been selected for their insulin secretion profile in response to glucose and to other physiological or pharmacological insulin secretagogues such as sulfonylureas and GLP-1. The cells are cultured in complete medium, RPMI 1640 10 mM glucose supplemented with 1 mM sodium pyruvate, 50 μM 2-mercaptoethanol, 2 mM glutamine, 10 mM HEPES, 100 IU/mL penicillin, 100 μg/mL streptomycin and 10% heat inactivated foetal calf serum (FCS), as described by Asfari et al. (23). For the insulin secretion assay, INS-1 cells are plated ($4.5 \times 10^4$ cells/well) and cultured in 96-well poly ornithine coated plates. After 3 days of culture at 37° C. in a humidified atmosphere of 95% air/5% CO2, the medium is removed and cells are cultured for 16 h in a medium containing 5 mM glucose, 1% FCS (and the tested drugs for long term evaluation).

The day of the insulin secretion test, the cells are washed with Krebs-Ringer Bicarbonate HEPES buffer (KRBH; pH 7.4) 0.1% Bovin Serum Albumin (BSA) and pre-incubated for 30 min at 37° C. in KRBH 0.1% BSA containing 2.8 mM glucose.

The cells are washed again with KRBH and incubated for 1 h in KRBH 0.1% BSA containing 3.5 mM glucose and the tested molecules. The supernatants are collected for insulin determination and lactate dehydrogenase (LDH) activity measurement.

Insulin Quantification

The insulin concentration in the collected supernatants is measured by an ELISA kit according to the manufacturer recommendations and using a rat insulin antibody (Insulin rat high range ELISA Alpco Cat no 80-INSRTH-E10). Very briefly, rat monoclonal antibodies specific for insulin are immobilized to 96-well plates. Standards, samples and controls are added to the appropriate wells with a horseradish peroxidase enzyme-labeled monoclonal antibody (Conjugate). After incubation, the microplates are washed to remove unbound conjugate and a TMB Substrate solution is added to react with the bound conjugate. Finally, after addition of a stop solution, the optical density is measured at 450 nm using a reference wavelength of 620 nm. The intensity of the yellow color is directly proportional to the amount of insulin within the samples.

The efficacy of the drugs is demonstrated by evaluating the quantity of insulin (expressed in pmol/L) secreted in absence or presence of drugs of the invention in the medium.

Results

Figure 2:
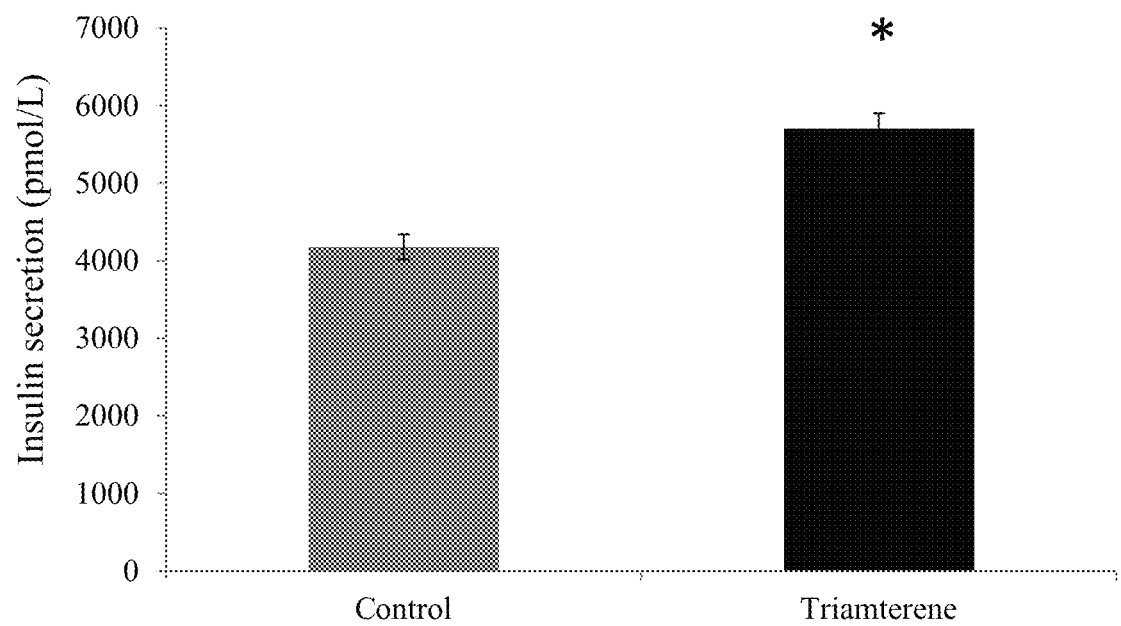
FIG. 2: Effect of triamterene short term pre-treatment on insulin secretion in INS-1 cells. The insulin secretion is significantly enhanced by triamterene (+37%).
Figure 3:
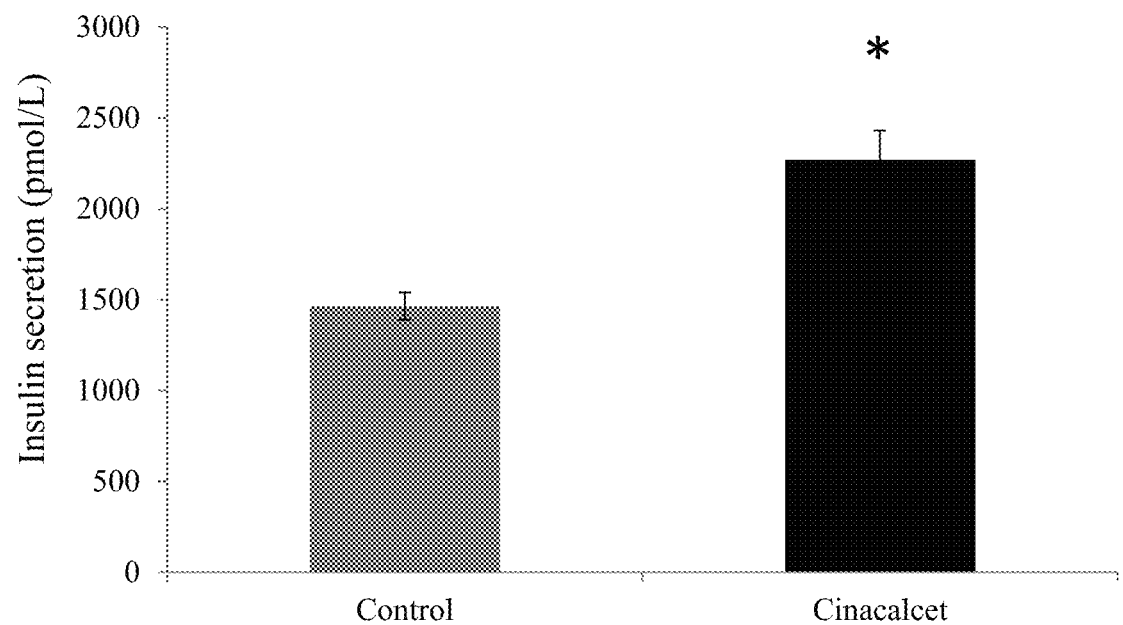
FIG. 3: Effect of cinacalcet long term pre-treatment on insulin secretion in INS-1 cells. The insulin secretion is significantly enhanced by cinacalcet (+55%) at doses as low as 1 µM.

Drugs of the invention induce an insulin secretion in response to glucose stimulation. For example, FIGS. 2 and 3 show that triamterene (10 µM, +37%) and cinacalcet (1 µM, +55%) respectively, can significantly enhance the secretion of insulin in response to glucose stimulation, following respectively a short term or long term incubation.

1.3 Glucose Uptake in Muscles or Adipocytes 1.3.1 Glucose Uptake in Mouse Muscle Cells Drugs of the invention have been tested in several models for insulin resistance. Glucose uptake enhancing capacities of compositions of the invention were measured both in muscle cells and in adipocytes either in normal or in pathological conditions. Depending on culture conditions, the muscle cells either exhibit continuous mitosis or alternatively terminally differentiate into myotubes.

Cell Culture and Media

Mouse muscle cells H-2 Kb, are grown for 4 days on 24-well plates coated with matrigel at a density of $0.8 \times 10^4$ cells/well under permissive conditions (33° C. in a humidified atmosphere of 95% air/10% $CO_2$; DMEM 5.5 mM D-glucose supplemented with 20% FCS, 10% horse serum, 2% glutamine, 0.5% chicken embryo extract, 20 mU/mL mouse INFγ, 100 U/mL penicillin, and 100 µg/mL streptomycin) as described previously by Fryer et al. (25). For differentiation in myoblast, cells are switched to non-permissive culture conditions (37° C. in a humidified atmosphere of 95% air/5% $CO_2$; DMEM 5.5 mM D-glucose supplemented with 2% FCS, 10% horse serum, 2% glutamine, 1% chicken embryo extract, 100 U/mL penicillin, and 100 µg/mL streptomycin).

Glucose Uptake

For long term effect evaluation, the day before glucose uptake assay, cells are incubated in DMEM 5.5 mM D-glucose supplemented with 10% horse serum, 2% SVF, 1% chicken embryo extract, 2% glutamine in the presence of the tested molecules for 16 h. The day after, and prior to the test, cells are washed and incubated in the presence of the tested molecules for 4 h more, in a serum-free medium {DMEM) containing 5.5 mM D-glucose.

For short term effect evaluation, 4 hours prior to the glucose test, cells are washed and incubated in a serum-free medium (DMEM) containing 5.5 mM D-glucose and the tested molecules. Then glucose uptake is measured by incubation of the cells for 5-10 min with radiolabelled 2-deoxy-D-[1,2 $^3$H] glucose in Krebs-Ringer HEPES buffer (KRBH; pH 7.4) 0.1% Bovine Serum Albumine (BSA) fraction V (Sigma_A-4503). Glucose uptake is arrested by two washing steps in ice-cold NaCl 0.9%. Then cells are solubilized in 0.1N NaOH for 30 min. Cell associated radioactivity is then counted and protein quantification is determined using the colorimetric Lowry method. Glucose uptake is estimated by measuring the radioactivity incorporated to the cells by a MicroBeta counter after adding 600 µL per well of scintillant (Optiphase SuperMix3).

Protein quantification is performed by a colorimetric assay derived from Lowry method.

Results are expressed in nmol glucose incorporated/5 min/mg protein and in % of control or basal condition (100%).

Results

Figure 4:
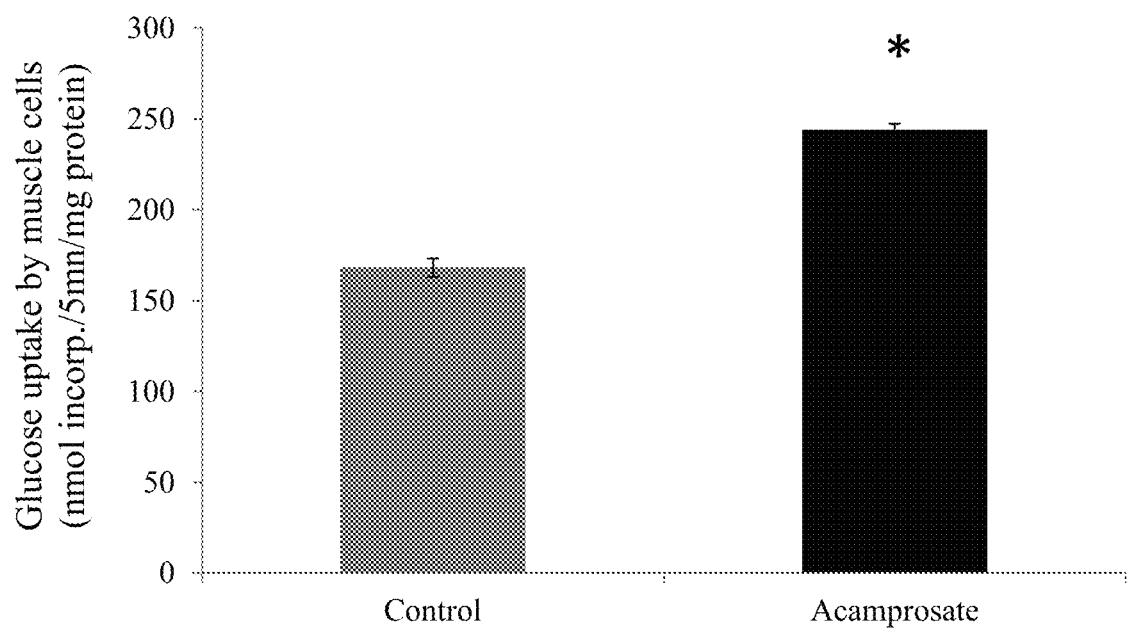
FIG. 4: Effect of acamprosate short term pre-treatment on glucose uptake in H-2 Kb cells. The glucose uptake is significantly enhanced by acamprosate (+45%) at doses as low as 0.1 µM.
Figure 5:
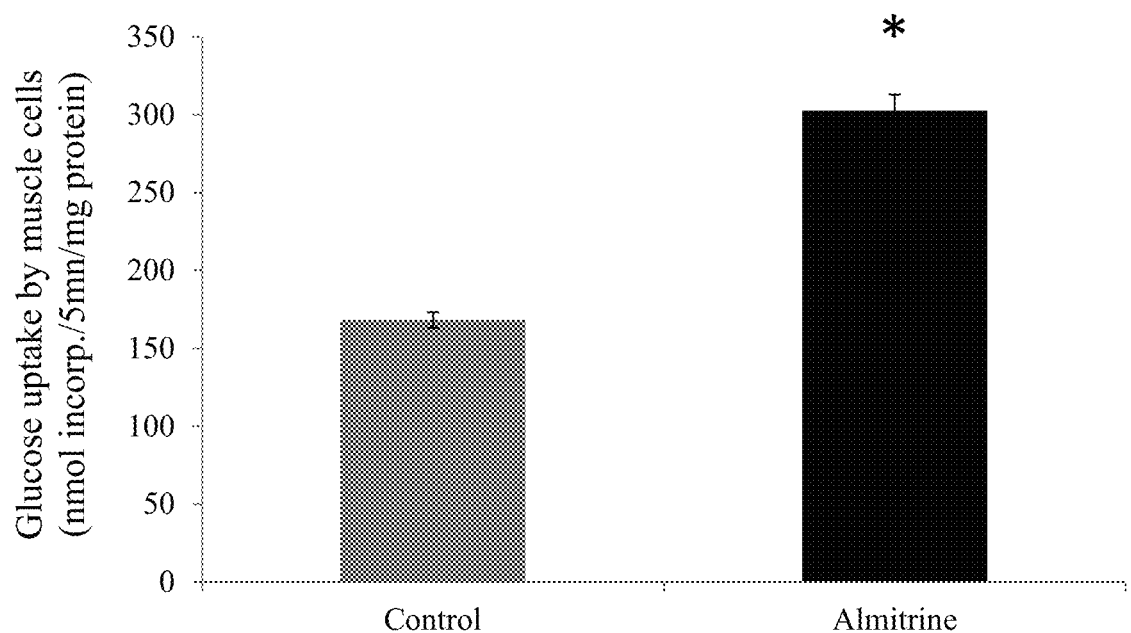
FIG. 5: Effect of almitrine short term pre-treatment on glucose uptake in H-2 Kb cells. The glucose uptake is significantly enhanced by almitrine (+80%) at doses as low as 1 µM.
Figure 6:
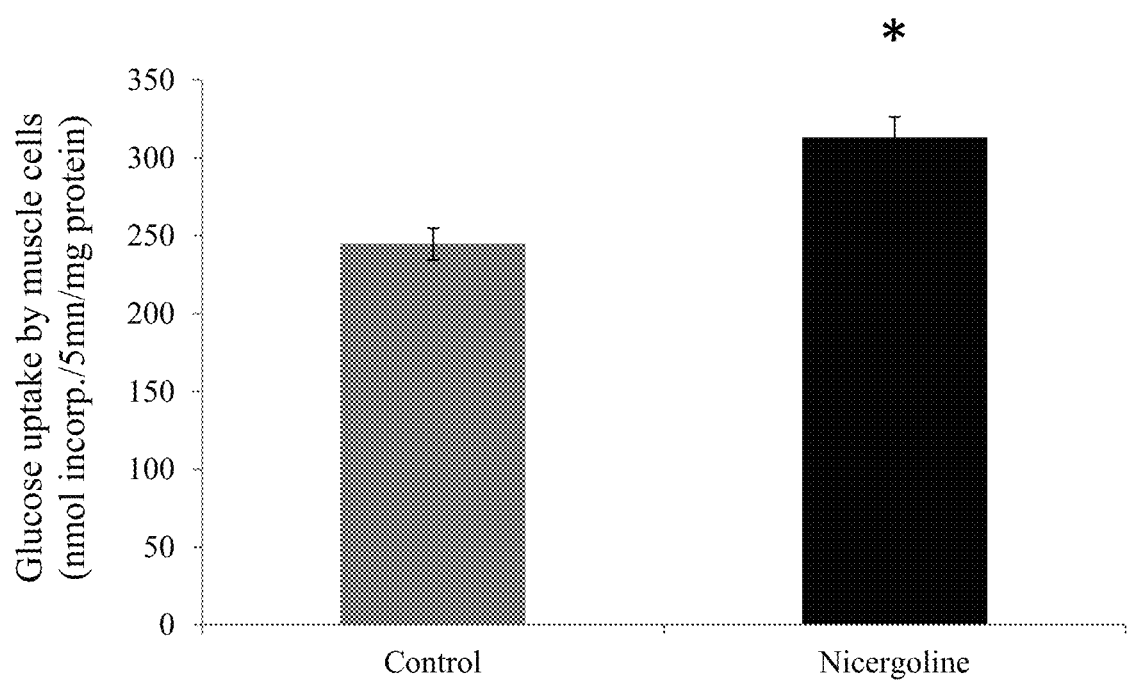
FIG. 6: Effect of nicergoline long term pre-treatment on glucose uptake in H-2 Kb cells. The glucose uptake is significantly enhanced by nicergoline (+28%).

Drugs of the invention, tested alone, can enhance glucose uptake in muscle cells. For example, FIGS. 4, 5 and 6 show that the glucose uptake by muscle cells H-2 Kb is significantly enhanced after short term incubation with acamprosate (0.1 µM, +45%) and almitrine (1 µM, +80%) or after long term incubation by nicergoline (10 µM, +28%) respectively, when compared to non-treated muscle cells.

1.3.2 Glucose Uptake in Human Diabetic Myotubes Primary Cultures

In order to have a model that is most reflective of the diabetic pathological conditions, efficiency of drugs in enhancing glucose uptake in diabetic myotubes was tested. Indeed, it has been demonstrated that the diabetic phenotype is conserved in myotubes established from diabetic subjects.

Cell Culture and Media

The myotubes from a diabetic patient were grown on HAM's F10-based media (Sigma, ref N6908) supplemented with 15% of fetal bovine serum, 1 mM glutamine.

Myoblast were seeded at 380,000 cells/well in 12-well plates. After 2 days of proliferation, the cells were placed in reduced serum conditions (2% horse serum) to induce differentiation. The myotubes were used after 5 days of differentiation.

Dulbecco's modified Eagle's medium (DMEM)-based media (Gibco, ref 31053-028) supplemented with 2% heat-inactivated Horse serum, 2% Glutamax (Gibco, 35050) and washed for glucose uptake assays. Compounds were dissolved in DMSO to reach desired final concentration prior use.

The differentiated myotubes were treated for 24 h with the compositions of the invention, before the assay.

Glucose Uptake Assay

Before the initiation of glucose uptake, the cells were deprived of serum and glucose. A deprivation was first performed in DMEM media containing reduced glucose (1 g/L) and no serum. After adding the compounds at the desired concentrations, the cells were incubated at 37° C. during 2 h30. The control with insulin allows the measurement of glucose uptake induction through the insulin pathway. Insulin treatment (100 nM) was done during 30 min at 37° C. A subsequent glucose and serum deprivation was performed in FIBS buffer at 37° C. for 2 hours. The cells were treated with a mixture of 2-[$^3$H]deoxyglucose 10Ci/mM+2-deoxy-D-glucose at 10 µM for 30 min. The cells were rinsed twice with 1 mL of cold PBS. The lysis was performed in 500 µL of 0.05N NaOH for 20 minutes. The cells lysates were transferred into scintillation vials for the measurement of radioactivity with a MicroBeta counter.

Results

Compositions of the invention can enhance glucose uptake in human primary myotubes. For example, FIGS. 13, 14, 15, 16 and 17 show that the glucose uptake in diabetic myotubes is improved after pre-incubation by torasemide (+24%, 18% respectively at 0.01 µM and 0.1 µM p<0.01; and +14% at 1 µM p<0.05), fenspiride (+34%, +30%, respectively at 0.01 µM respectively at 0.01 µM, 0.1 µM and 1 µM, p<0.05), ifenprodil (+48% at 0.01 µM, p=0.07; and improvement at 0.1 µM and 1 µM) and triamterene (0.01 µM, +13%, p<0.05).

Figure 28:
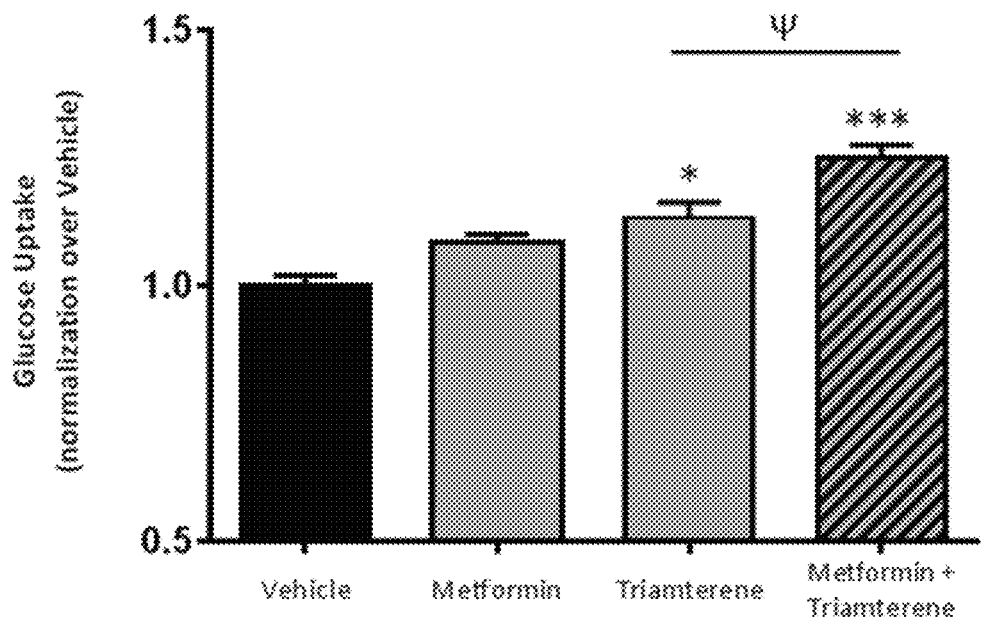
FIG. 28: Enhanced effect of triamterene-metformin combinatory treatment on glucose uptake in human primary myotubes derived from a diabetic patient. Glucose uptake is significantly enhanced by triamterene-metformin combination (+125%) when compared to the non-treated myotubes (Dunnett's test, ***p<0.001) at concentrations as low as 0.01 µM for triamterene and 60 µM for metformin. Glucose uptake is significantly higher in myotubes pretreated with the combination than in cells treated with the single drugs (grey bars, t-test, ψ: p<0.05; Dunnett's test, *p<0.05).
Figure 29:
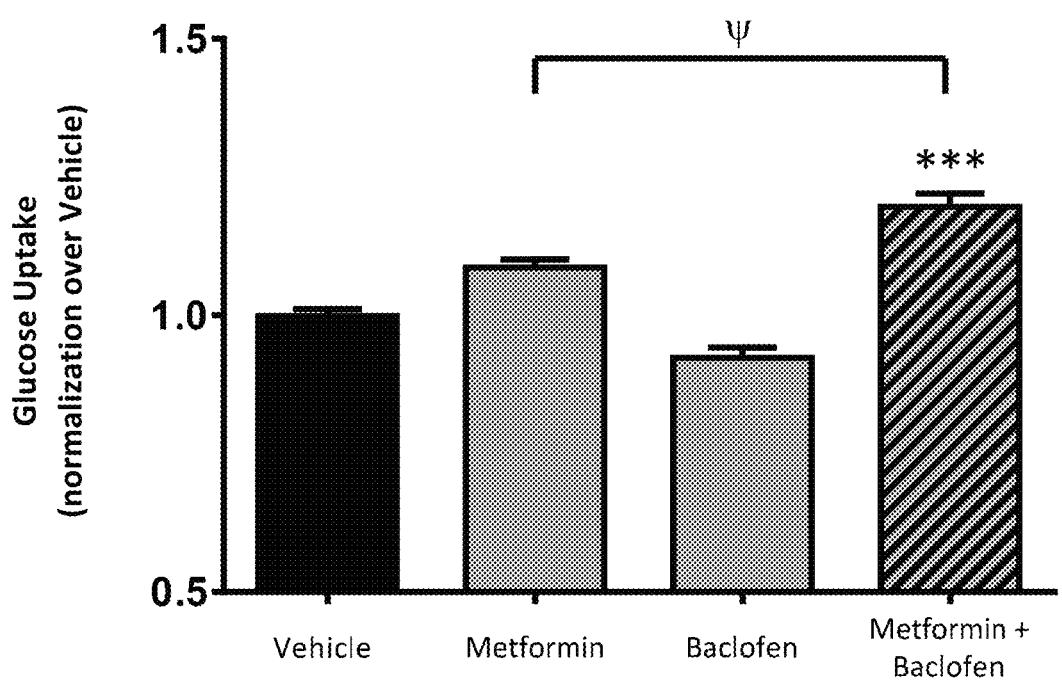
FIG. 29: Enhanced effect of baclofen-metformin combinatory treatment on glucose uptake in human primary myotubes derived from a diabetic patient. Glucose uptake is significantly enhanced by baclofen-metformin combination (+120%) when compared to the non-treated human primary myotubes (Dunnett's test, ***p<0.001) at concentration as low as 0.37 nM for baclofen and 60 µM for metformin). Glucose uptake is significantly higher in myotubes pretreated with the combination than in cells treated with the single drugs (grey bars, t-test, ψ: p<0.05).

Drugs of the invention can also be advantageously combined with metformin to produce an enhanced effect on insulin resistance. As exemplified in FIGS. 28 and 29, triamterene and baclofen exert a surprisingly significant enhancing effect on metformin treatment leading to an improvement of glucose uptake of 125% and of 120% as compared to non-treated insulino resistant myotubes, said uptake being significantly improved as compared to glucose uptake levels with drugs used alone, which demonstrates an unexpected superiority of these combinatorial treatments. As exemplified, such an enhancing effect allows using doses of metformin which, alone, are no or barely effective and obtaining a significant improvement of glucose uptake. This allows alleviating or delaying side effects usually observed for antidiabetic treatments, and more particularly for biguanides and even more particularly for metformin.

1.3.3 Glucose Uptake in Adipocytes Cells 3T3-L1

3T3-L1 cells are fibroblasts which, under appropriate conditions, differentiate into adipocytes-like cells. These cells are used to show that compositions of the invention increase the glucose uptake in adipocytes, when compared to controls.

Cell Culture and Differentiation

3T3-L1 preadipocyte cells were cultured in DMEM containing 1% penicillin-streptomycin (PS) and 10% bovine calf serum at 37° C. in a 5% $CO_2$ atmosphere. To induce differentiation, 2-day post-confluent preadipocytes were cultured in MDI differentiation medium I (DMEM containing 1% PS, 10% FBS, 0.5 mM IBMX, 1 µM dexamethasone, 0.5 µg/mL insulin) for 2 days. Differentiation, as measured by the expression of adipogenic markers and the appearance of lipid droplets, usually reaches completion between days 4 and 8.

Glucose Uptake Activity Assay

Glucose uptake activity was analyzed by measuring the uptake of radiolabeled glucose. Differentiated 3T3-L1 adipocytes grown in 12-well plates were washed twice with serum-free DMEM and incubated for 2 h at 37° C. with 1 mL DMEM containing 0.1% BSA. The cells were washed three times with Krebs-Ringer-HEPES (KRH) buffer (20 mM HEPES, pH 7.4, 136 mM NaCl, 4.7 mM KCl, 1.25 mM $MgSO_4$, 1.25 mM $CaCl_2$, 2 mg/mL bovine serum albumin), and incubated at 37° C. for 30 min with 0.9 mL of KRH buffer.

Next, cells were incubated with or without drugs for different duration in order to evaluate their effect in short term and long term.

To evaluate their short term effect, cells were incubated with drugs of the invention for 4 hours at 37° C. To evaluate the long term effect of drugs of the invention, the day prior to the test, cells were pre-incubated with or without drugs for 16 h. The day after, and prior to the test, cells were washed and incubated in the presence of the tested molecules for 4 h more.

Glucose uptake was initiated by the addition of 0.1 mL of KRH buffer containing 2-deoxy-D-[$^3$H] glucose (37 MBq/L) and glucose (1 mM). After 20 min, glucose uptake was terminated by washing the cells three times with cold PBS. The cells were lysed through incubation for 20 min at 37° C. with 0.7 mL of Triton X-100. Level of radioactivity in the cell lysates was determined using a scintillation counter.

Protein quantification was performed by a colorimetric assay derived from LOWRY method.

Results are expressed in nmol glucose incorporated/5 min/mg protein and in % of control or basal condition (100%).

Results

Figure 7:
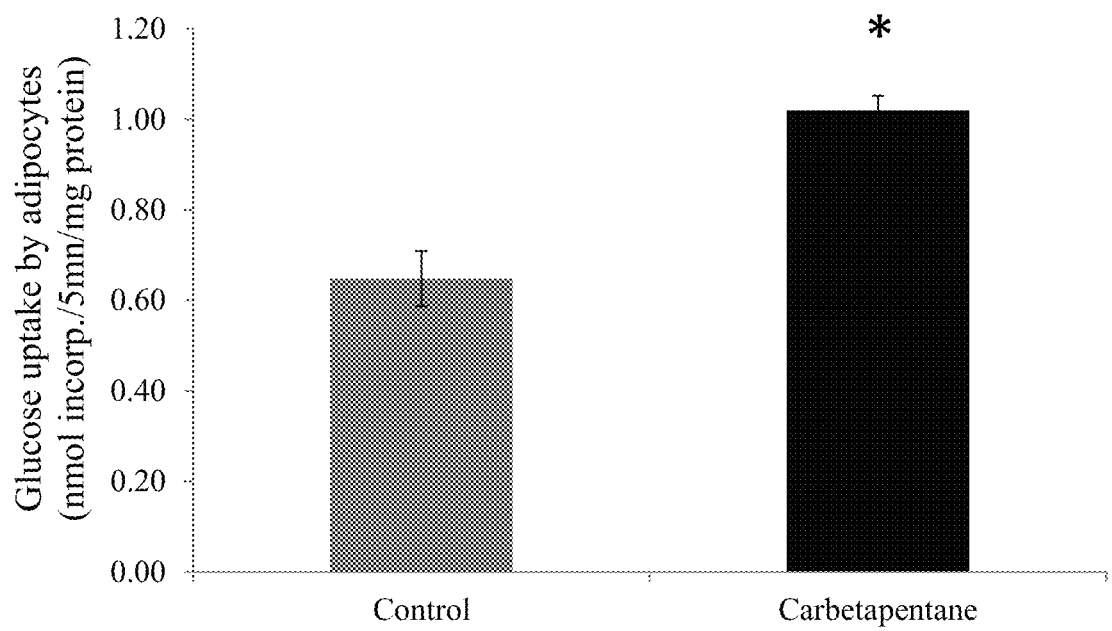
FIG. 7: Effect of carbetapentane short term pre-treatment on glucose uptake in 3T3-L1 cells. The glucose uptake is significantly enhanced by carbetapentane (+58%) at doses as low as 100 nM.
Figure 8:
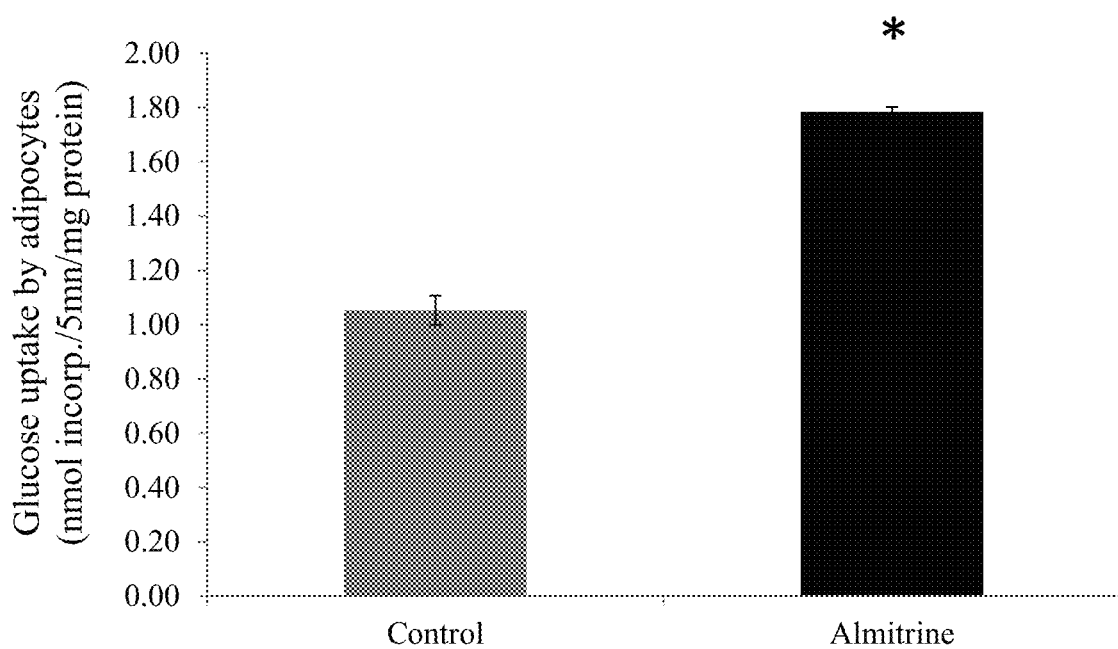
FIG. 8: Effect of almitrine long term pre-treatment on glucose uptake in 3T3-L1 cells. The glucose uptake is significantly enhanced by almitrine (+69%) at doses as low as 1 µM.
Figure 12:
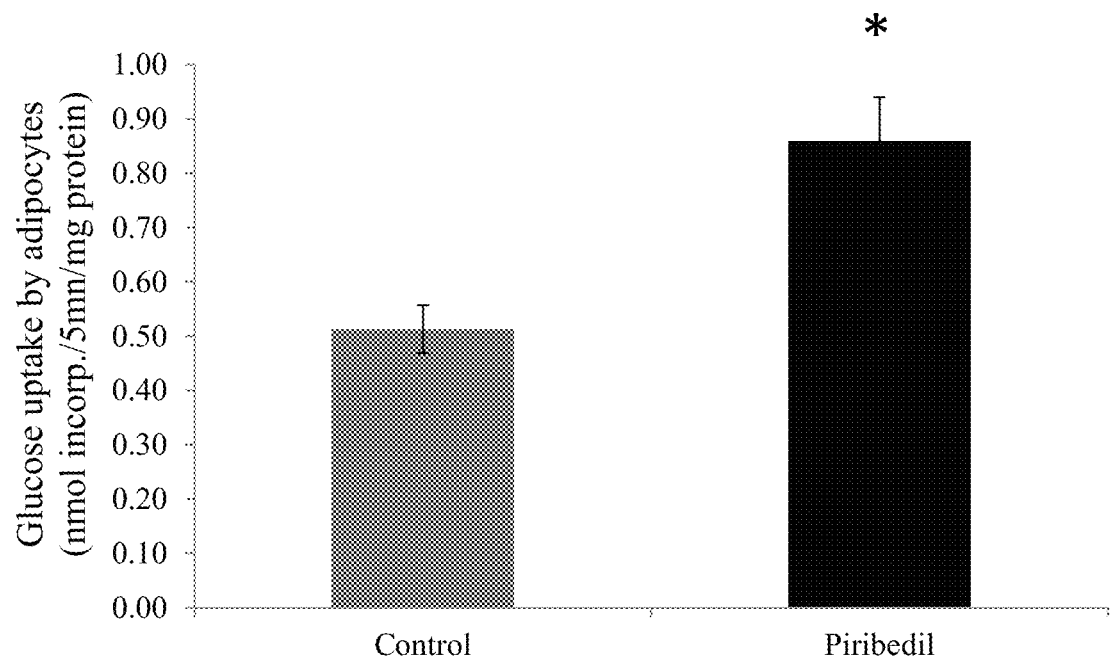
FIG. 12: Effect of piribedil short term pre-treatment on glucose uptake in 3T3-L1 cells. The glucose uptake is significantly enhanced by piribedil (+68%) at doses as low as 10 nM.
Figure 13:
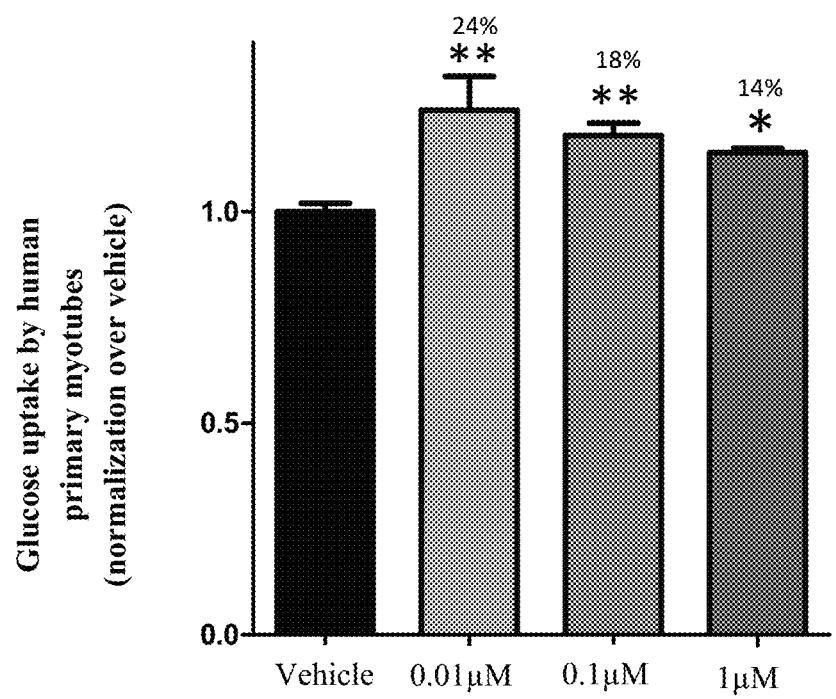
FIG. 13: Effect of torasemide pre-treatment on glucose uptake in human primary diabetic myotubes. The glucose uptake is significantly enhanced (+24%, +18% and +14% respectively) at doses as low as 0.01 µM, 0.1 µM and 1 µM.
Figure 14:
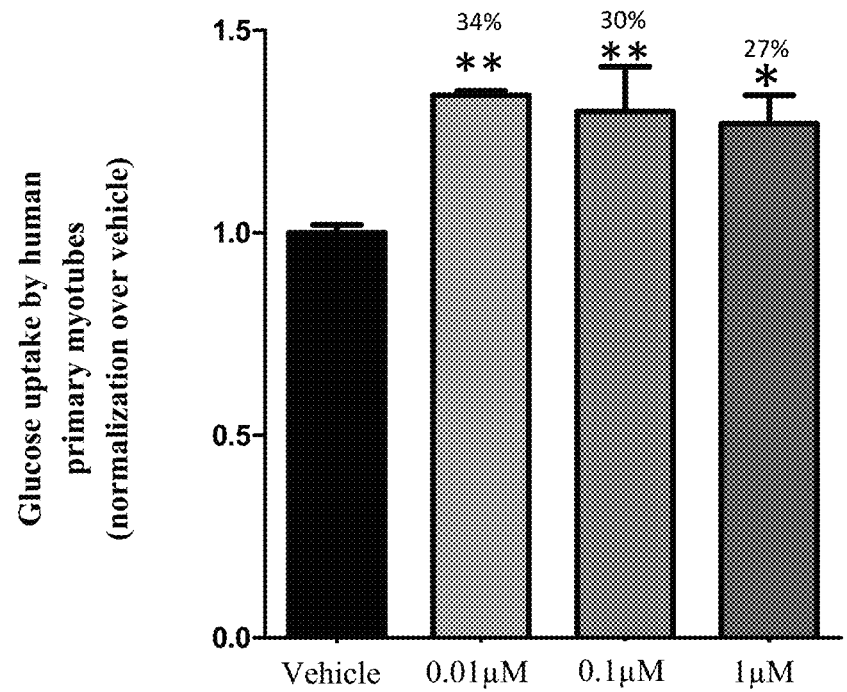
FIG. 14: Effect of fenspiride pre-treatment on glucose uptake in diabetic myotubes derived from a diabetic patient. The glucose uptake is significantly enhanced (+34%, +30%, +27% respectively) at doses as low as 0.01 µM, 0.1 µM and 1 µM.
Figure 15:
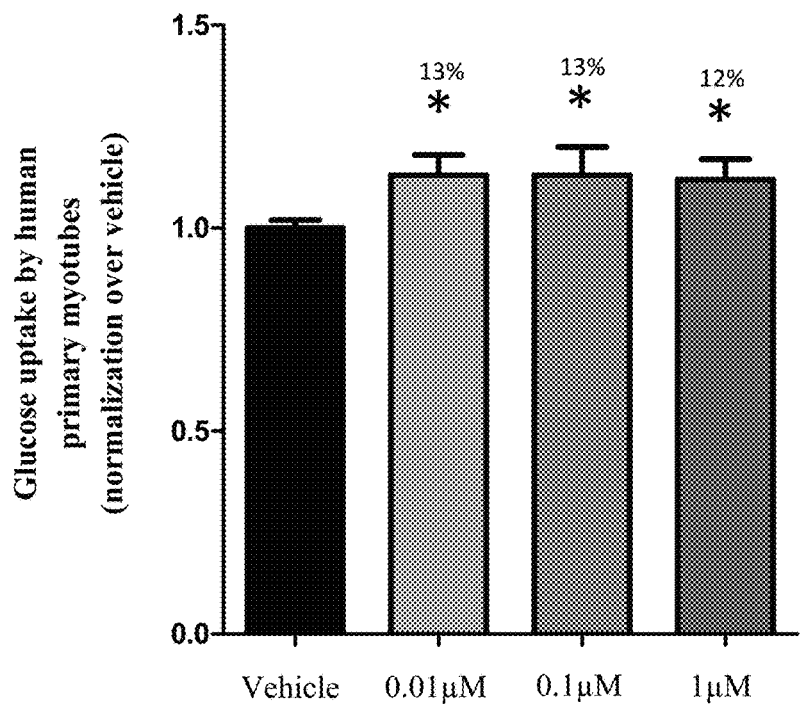
FIG. 15: Effect of tolfenamic acid pre-treatment on glucose uptake in human primary myotubes derived from a diabetic patient. The glucose uptake is significantly enhanced (+13%, +13% and +12% respectively) at doses as low as 0.01 µM, 0.1 µM and 1 µM.
Figure 16:
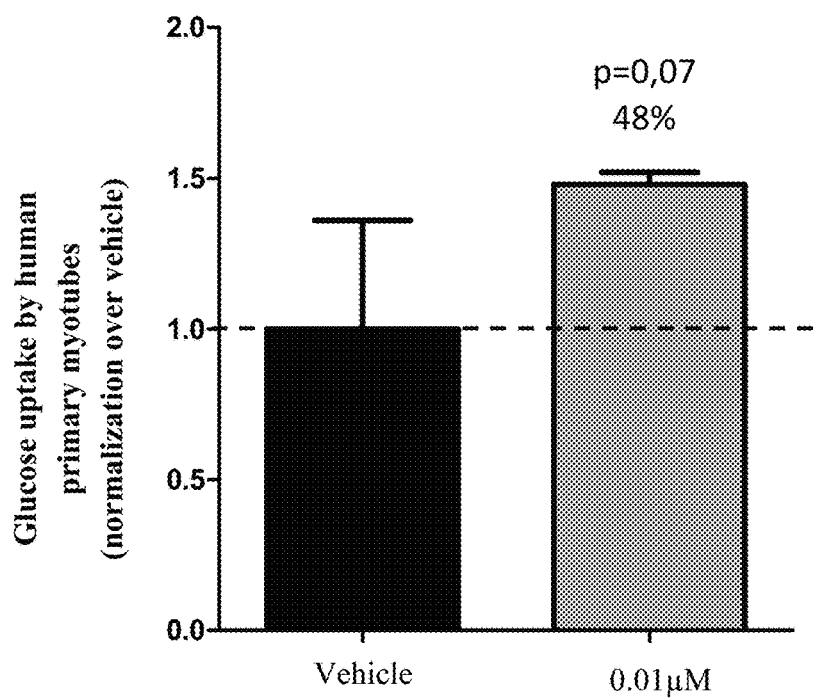
FIG. 16: Effect of ifenprodil pre-treatment on glucose uptake in human primary diabetic myotubes. The glucose uptake is enhanced (+48%) at doses as low as 0.01 µM.
Figure 17:
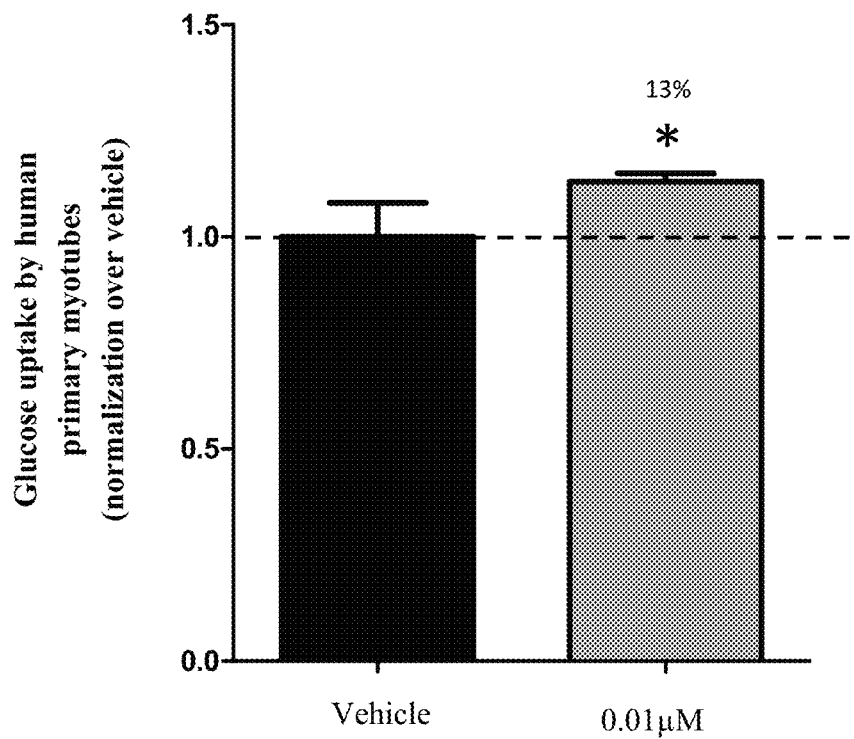
FIG. 17: Effect of triamterene pre-treatment on glucose uptake in human primary diabetic myotubes. The glucose uptake is significantly enhanced (+13%) at doses as low as 0.01 µM.
Figure 18:
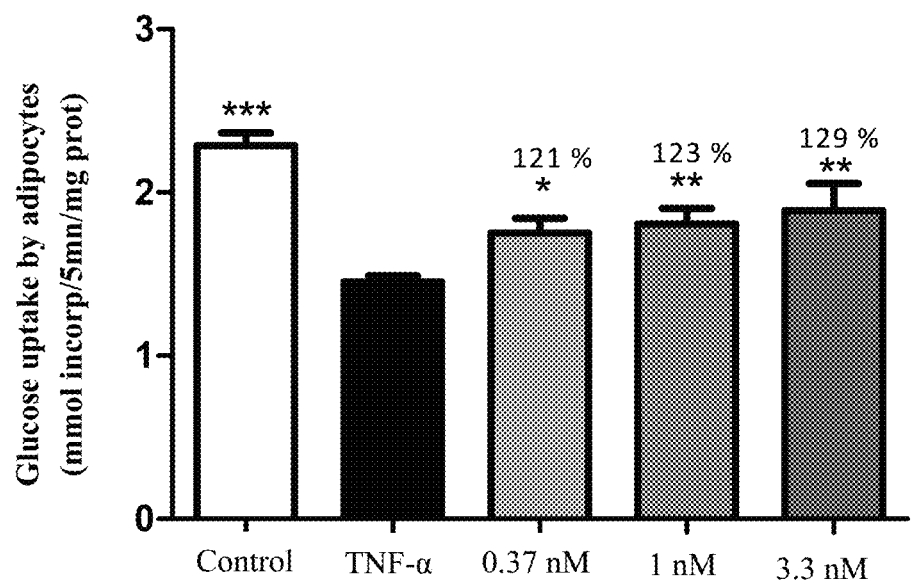
FIG. 18: Effect of torasemide pre-treatment on glucose uptake by 3T3L1 differentiated adipocytes, under TNF-α induced insulin resistance condition. The glucose uptake is significantly enhanced (+121%, +123% and +129%, respectively) at doses as low as 0.37 nM, 1 nM and 3.3 nM, when compared to non-treated insulin resistant cells (TNFα).
Figure 19:
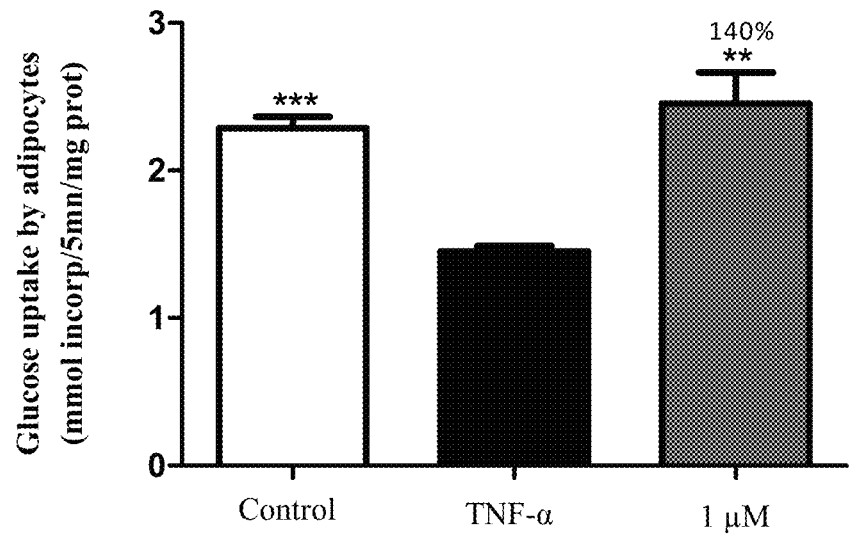
FIG. 19: Effect of ifenprodil pre-treatment on glucose uptake by 3T3L1 differentiated adipocytes, under TNF-α induced insulin resistance condition. The glucose uptake is significantly enhanced (+140%) at doses as low as 1 µM, when compared to non-treated insulin resistant cells (TNFα).
Figure 20:
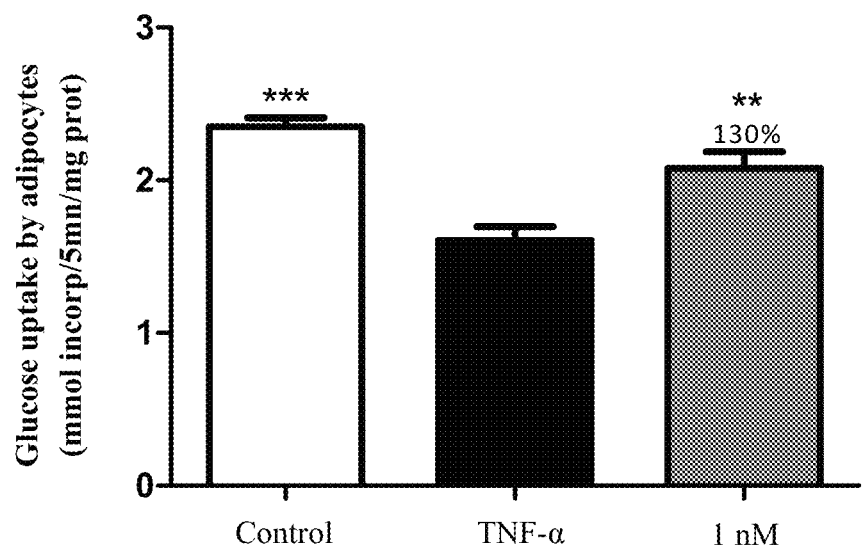
FIG. 20: Effect of fenspiride pre-treatment on glucose uptake by 3T3L1 differentiated adipocytes, under TNF-α induced insulin resistance condition. The glucose uptake is significantly enhanced (+130%) at dose as low as 1 nM, when compared to non-treated insulin resistant cells (TNFα).
Figure 21:
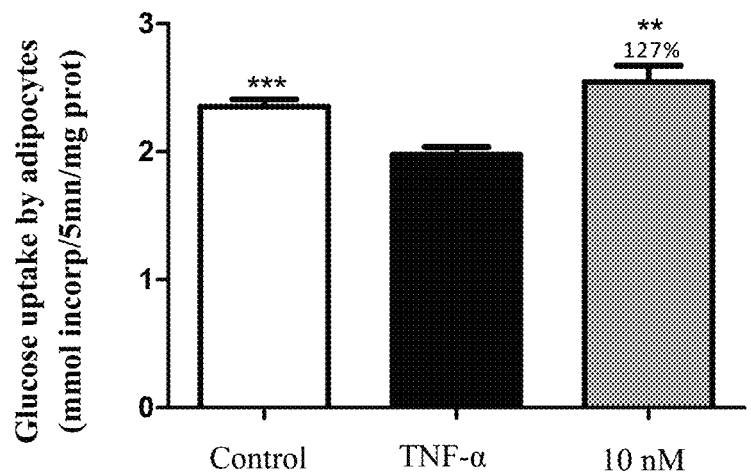
FIG. 21: Effect of tolfenamic acid pre-treatment on glucose uptake by 3T3L1 differentiated adipocytes, under TNF-α induced insulin resistance condition. The glucose uptake is significantly enhanced (+127%) at dose as low as 10 nM, when compared to non-treated insulin resistant cells (TNFα).

Drugs of the invention can enhance glucose uptake in adipocytes. For example, FIGS. 7, 12 and 8 show that the glucose uptake by differentiated 3T3-L1 adipocyte cells can be enhanced after short term incubation by carbetapentane (0.1 µM, +58%) and piribedil (10 nM, +68%) or after long term incubation by almitrine (1 µM, +69%) respectively.

1.3.4 Glucose Uptake in TNFα Induced Insulin Resistant 3T3-L1 Differentiated Adipocytes To evaluate capacities of drugs of the invention to improve glucose uptake by adipocytes in insulin resistant conditions, cells were pretreated by TNF-α. Upon TNF-α exposure, a decrease in glucose uptake in response to insulin is expected. By contrast, an increase in glucose uptake in response to insulin is expected after treatment of the 3T3-L1 cells with TNF-α and acetylsalicylic acid (positive control).

Cell Culture and Differentiation

3T3L1 fibroblasts were maintained in DMEM 4.5 g/L glucose supplemented with 5% calf serum donor, 5% new born calf serum, 100 U/mL penicillin, and 100 µg/mL streptomycin at 37° C. under a 10% $CO_2$ atmosphere. Cells were grown on 24 well plates at a density of 2560 cells/well in 0.5 mL of growth medium (DMEM 4.5 g/L glucose supplemented with 10% FCS, 100 U/mL penicillin, and 100 µg/mL streptomycin). Five days after plating (90% of confluence), the induction of adipocytes differentiation was carried out in DMEM 4.5 g/L glucose containing 10% FBS, IBMX 100 µM, dexamethasone 0.25 µM and insulin 170 nM. Two days after, the induction medium was removed and changed by DMEM 4.5 g/L glucose containing 10% FBS and insulin 170 nM. Fresh medium were replaced after two days. Three days after, the adipocytes were incubated overnight in fasting medium (DMEM 4.5 g/L glucose containing 0.2 SVF, 100 U/mL penicillin, 100 µg/mL streptomycin. Then, the cells were treated with $H_2O$ or 5 ng/mL of rat TNF-α (Peprotech, 400-14) for 48 h in DMEM 4.5 g/L glucose containing 10% FBS. The medium was refreshed every day. Glucose uptake was assayed in different conditions: the adipocytes were treated for the further 24 h with 0.1% DMSO with or without 5 ng/mL TNF-α, or with 5 ng/mL TNF-α and 5 mM acetylsalicylic acid, or with 5 ng/mL TNF-α and 100 nM insulin, or the tested compounds with 5 ng/mL TNF-α in the presence or absence of insulin (100 nM) as described below.

Glucose Uptake Activity Assay

Glucose uptake was measured by quantification of incorporated radiolabelled glucose, after an incubation step with 2-deoxy-D[1,2$^3$H] glucose for 5 min. Glucose uptake was arrested by two washing steps in ice-cold PBS 1×. Then were solubilized in 0.1N NaOH for 30 min. Cell associated radioactivity have been then counted by using a MicroBeta counter after adding 600 µL per well of scintillant (Optiphase SuperMix3).

In parallel, protein quantification was determined by a colorimetric assay derived from LOWRY method. Results are expressed in nmol of glucose incorporated/5 min/mg of protein and in % of control or basal condition (100%).

To assess cell viability, a LDH activity measurement was performed on the supernatants by using an UV method with the commercial kit (ABS pentra LDH IFCC CP, ref A11A01871). Very briefly, LDH reduces $NAD^+$ to NADH by oxidation of lactate to pyruvate. The NADH produced were evaluated by measurement of the absorbance at 340 nm. The amount of NADH produced is proportional to the amount of LDH released in the culture medium as a result of cytotoxicity. Cell viability results are expressed in % of control or basal condition (100%).

Results

Drugs of the invention, tested alone, enhance glucose uptake in adipocytes in insulin resistance mimicking conditions. For example, FIGS. 18, 19, 20 and 21 show that the glucose uptake by TNF-α induced insulin resistant 3T3-L1 adipocytes is significantly enhanced after long term incubation by torasemide (+121% at 0.37 nM, p<0.05; +123% and +129%, respectively at 1 nM and 3.3 nM, p<0.01), ifenprodil (+140% at 1 µM, p<0.01; and improvement at 10 nM and 100 nM, not shown), fenspiride (+130% at 1 nM, p<0.01; and improvement at 0.37 nM and 3.3 nM, not shown) and tolfenamic acid (+127% at 10 nM, p<0.01; and improvement at 100 nM and 1 µM, not shown).

Drugs of the invention also exert an enhancing effect on antidiabetic treatments. As exemplified in FIGS. 24-27, torasemide, triamterene, baclofen and tolfenamic acid exert a surprising significant enhancing effect on metformin treatment. In spite of the use of sub effective doses, combinations of metformin with compounds of the invention lead to a significant improvement of glucose uptake ranging from 127% to 144% when compared to non-treated cells, whereas none of metformin or of drugs of the invention leads to any significant improvement when used alone at the same concentrations, thereby sustaining an unexpected superiority of these combinatorial treatments. Using sub therapeutic doses of anti-diabetic chronic treatments with the compounds of the invention allows to alleviate or to delay the side effects usually observed for these antidiabetic treatments.

Results of section 1.3 show that drugs of the invention are efficient in improving glucose uptake in normal muscle cells and adipocytes as well as in insulin resistance mimicking conditions.

1.4 Glucose Production by Hepatic Cells
Cell Culture and Differentiation

Hepatocytes are isolated from 24 h-fasted male Wistar rats (200-250 g body weight) by ex situ liver perfusion in the presence of collagenase. Cell viability is validated by a trypan blue exclusion test. Then, cells are suspended in William's medium supplemented with insulin and seeded onto six-well plates (8 $10^5$ cells/well) and incubated at 37° C. in a humidified atmosphere of 95% air/5% $CO_2$. After plating, the medium is removed and cells are cultured for 16 h in RPMI medium without glucose (supplemented with the tested drugs for long term evaluation). The following day, hepatic glucose production test is assessed in Krebs-Ringer Bicarbonate HEPES buffer (KRBH; pH 7.4) in the presence of the neoglucogenic substrates (lactate 10 mM and pyruvate 1 mM) and the tested molecules for 4 h (short term).

Glucose Quantification

Supernatants are collected and glucose concentrations are determined using a Glucose Oxidase kit (Instrumentation laboratory 0018250840). In parallel, protein quantification is performed using the colorimetric Lowry method.

Results are expressed in nmol glucose/mg protein and % of control condition (KLP: KRBH containing lactate and pyruvate).

Results

Figure 9:
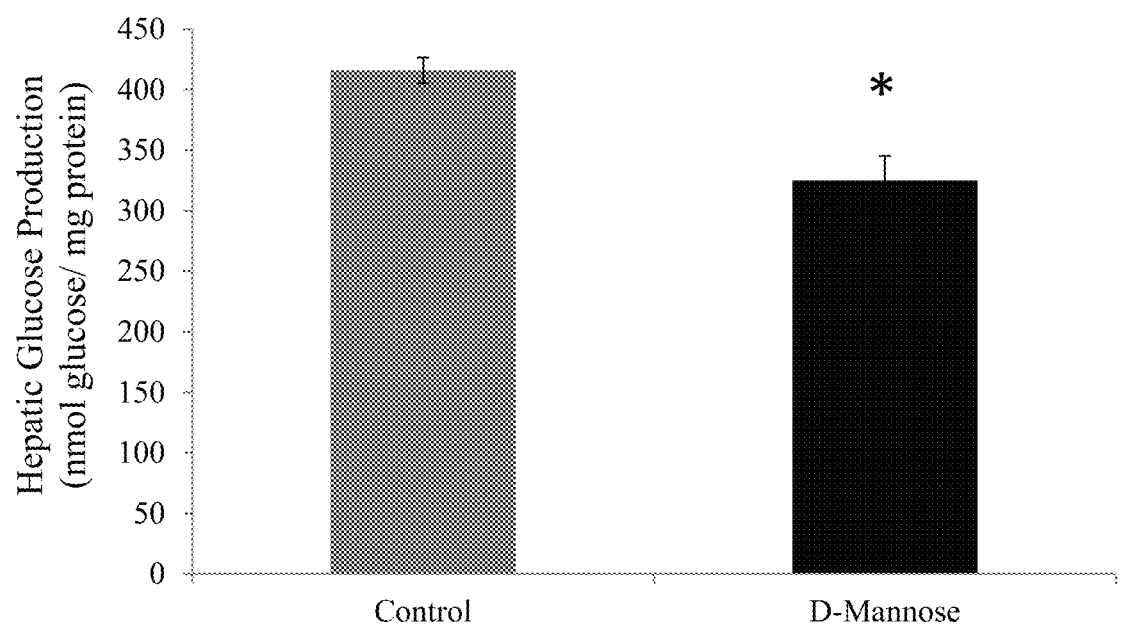
FIG. 9: Effect of D-mannose short term pre-treatment on glucose production by hepatic cells. The glucose production is significantly reduced by D-mannose (−22%).
Figure 10:
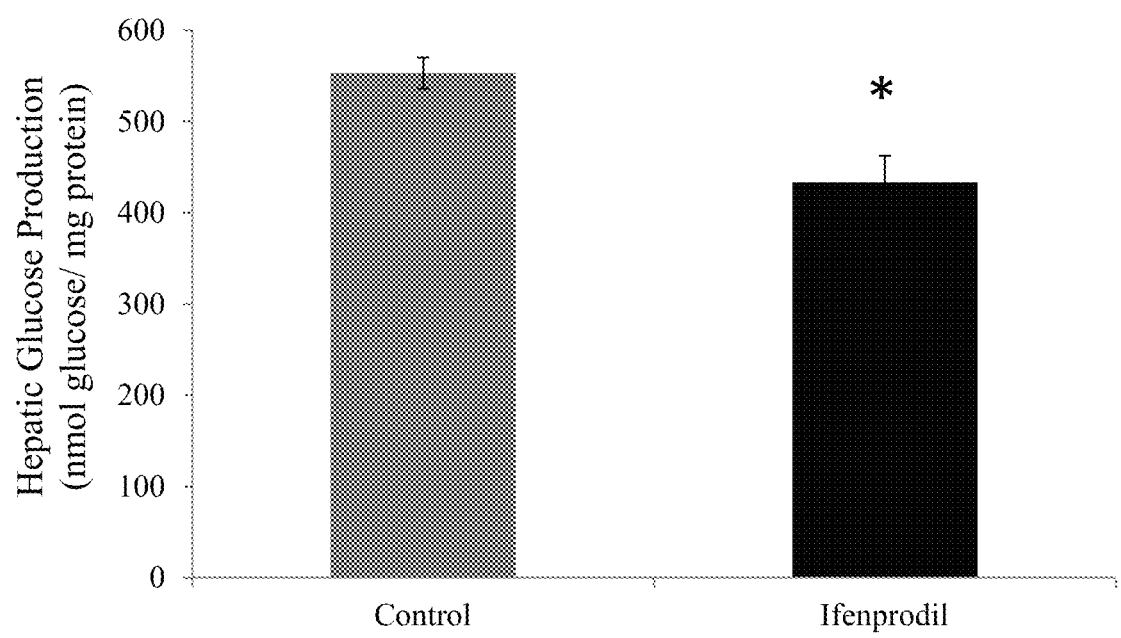
FIG. 10: Effect of ifenprodil long term pre-treatment on glucose production by hepatic cells. The glucose production is significantly reduced by ifenprodil (−22%) at doses as low as 10 nM.
Figure 11:
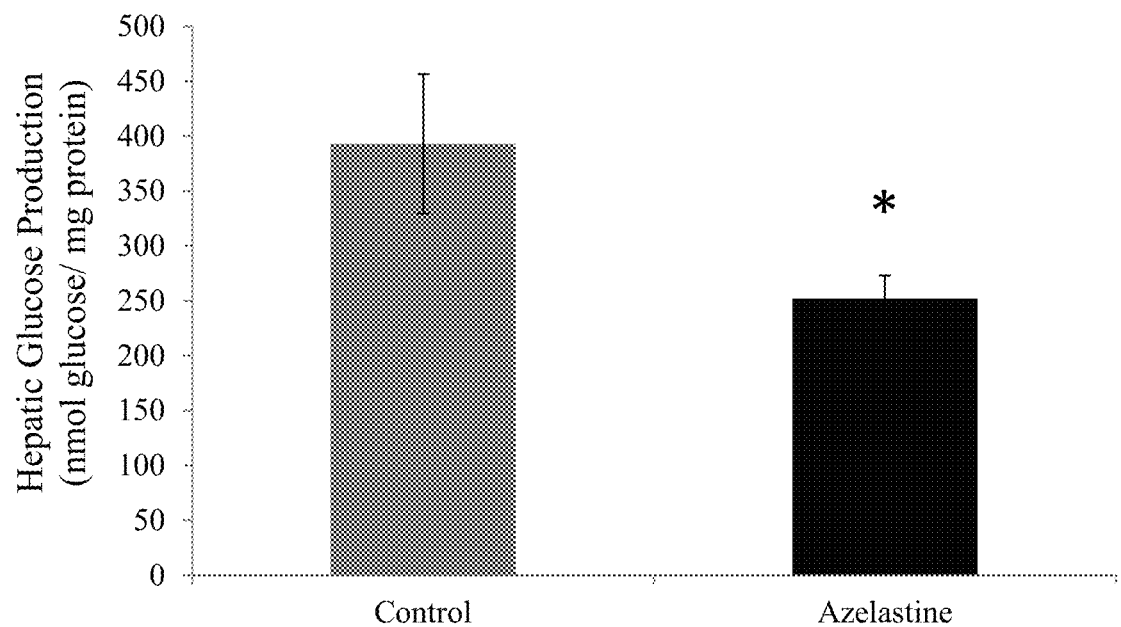
FIG. 11: Effect of azelastine long term pre-treatment on glucose production by hepatic cells. The glucose production is significantly reduced by azelastine (−36%).

Drugs of the invention, tested alone, can lower glucose production by hepatic cells. For example, FIGS. 9, 10 and 11 show that the glucose production by hepatocytes is significantly reduced after short term treatment by D-mannose (10 µM, −22%) or after long term treatment by ifenprodil (0.01 µM, −22%) or Azelastine (10 µM, −36%).

1.5 Isolated Organs
1.5.1 Insulin and Glucagon Secretion in Isolated Islets of Langerhans Isolated islets incubated with a range of glucose concentrations show a dose-dependent pattern of insulin release. Thus, the use of isolated islets is a physiological way of investigating the effects of candidate compounds as initiators and potentiators of insulin secretion.

Tissue Preparation

Rats are anesthetized by injection of ketamine/xylasine intra-peritoneal (ip). The peritoneal cavity is exposed and the pancreatic main duct to the intestine is clamped. The pancreas is then cannulated via the common bile duct, distended with collagenase and removed. Islets are extracted, washed and passed through a sterile stainless steel screen before being centrifuged. Islets are then cleaned and placed into CMRL medium containing 2 mM glutamine, 10% fetal bovine serum and 1% antibiotic/antimycotic solution and put into a 37° C. culture chamber containing 5% $CO_2$.

Islets Perfusion

Islets are preincubated for 90 min in RPMI 1640 medium containing 10% FBS and 3 mM glucose at 37° C. with 5% $CO_2$. The islets of control and treated groups are then incubated in the glucose perfusion system with a constant flow rate (500 µL/min) at 37° C. for 90 min. They are placed for 30 min in the basal conditions (3 mM glucose), for 30 min in a high glucose concentrated (20 mM) medium and finally for 30 min back in the basal conditions (3 mM glucose). Throughout the perfusion, samples of medium are collected from the output fraction and frozen at −80° C. At the end of the perfusion, the islets are harvested and frozen at −80° C. The total protein in the islets is extracted by acid ethanol (0.18 M HCl in 95% ethanol). Quantifications of the intracellular or released insulin and glucagon in the collected output fractions are realized by ELISA.

1.5.2 Glucose Uptake in Isolated Muscles
Muscle Incubation Procedure

Excised epitrochlearis are incubated at 29° C. for 50 min in 3 mL of continuously gassed (95% $O_2$, 5% $CO_2$) preincubation medium, consisting of Krebs-Henselheit bicarbonate buffer (KHB), 8 mM glucose, 32 mM mannitol and 0.1% bovine serum albumin (BSA). Following the preincubation, the muscle is transferred to another vial and incubated at 29° C. for 10 min in 3 mL of continuously gassed wash-out medium, consisting of KHB, 2 mM pyruvate, 38 mM mannitol and 0.1% BSA.

Finally, the muscle is incubated at 29° C. for 20 min in 3 mL of uptake medium, which consists of KHB, 2 mM pyruvate, 6 mM glucose, and 32 mM mannitol, 0.1% BSA, with or without 280 µCi/mmol [$^3$H] 2-deoxyglucose (2-DG) and 10 µCi/mmol [$^{14}$C]-mannitol and the designated treatment.

Immediately after incubation, muscles are briefly blotted on gauze wetted with 0.9% saline solution and freeze clamped in liquid nitrogen.

Muscle Glucose Uptake Measurements

Glucose uptake is calculated from the incorporation rate of 2-DG into the muscle fibers during the 20 min of incubation in the uptake medium. Frozen muscle samples are digested in 1 mL 1M KOH at 60° C. for 20 min. Muscle homogenates are neutralized with 1 mL 1 M HCl and 300 µL are added in a scintillation cocktail. Duplicate samples are counted for $^3$H and $^{14}$C in an LS-6000 liquid scintillation spectrophotometer.

Muscle 2-DG uptake is calculated as the difference between total muscle 2-DG and 2-DG in the extracellular space. 2-DG concentration in the extracellular space is determined by the amount of [$^{14}$C]-mannitol in the tissue.

1.5.3 Glucose Production from Isolated Perfused Liver

The model of the isolated perfused rat model allows studying direct effects on the intact organ without the influence from extra-hepatic hormones and other systemic alterations of metabolic fluxes.

Preparation of Tissue

Rats are anesthetized by ip injection of thiopental (50 mg/kg). Hemoglobin-free, non-recirculating perfusion is performed. After cannulation of the portal and cava veins, the liver is positioned in a plexiglass chamber. The perfusion fluid is Krebs/Henseleit-bicarbonate buffer (pH 7.4), saturated with a mixture of oxygen and carbon dioxide (95:5) by means of a membrane oxygenator with simultaneous temperature adjustment at 37° C. The flow, provided by a peristaltic pump, is between 30 and 33 mL/min. Candidate compounds or vehicle are added to the perfusion fluid after having supplemented the Krebs/Henseleit-bicarbonate buffer with fatty acid-free bovine serum albumin to ensure full dissolution of the drugs. For all concentrations of the drugs the molar albumin/drug ratio was equal to 2.4.

The cell viability of the perfused liver is judged from both the oxygen uptake rates and the perfusion fluid leakage from its surface. The livers are discarded when the oxygen uptake dropped to 0.7 µmol min$^{-1}$ g$^{-1}$ or when the surface fluid leakage surpassed 2.5% of the portal flow. Samples of the effluent perfusion fluid are collected and analyzed for their metabolite contents. The following compounds are assayed by means of standard enzymatic procedures: glucose, lactate and pyruvate. The oxygen concentration in the outflowing perfusate is monitored continuously, employing a Teflon-shielded platinum electrode adequately positioned in a plexiglass chamber at the exit of the perfusate. Metabolic rates are calculated from input-output differences and the total flow rates and are referred to the wet weight of the liver.

1.6 Results Synthesis

Table 4 gathers results that were obtained in all previously described models (see points from 1.1 to 1.5 above). A value is attributed to each candidate compound depending on its effect in the different in vitro models compared to vehicle. Results are normalized and weighed in order to generate a relative performance value for each candidate compound. A high value reflects a high potential of the compound for the normalization of glucose level and thus a significant efficacy for controlling glucose levels and/or for the treatment of diabetes or related disorders.

TABLE 4

| Drug Name | Relative performance value |
| --- | --- |
| acamprosate | 15 |
| almitrine | 38 |
| azelastine | 30 |
| baclofen | 16 |
| carbetapentane | 33 |
| cimetidine | 31 |
| cinacalcet | 32 |
| dexbromopheniramine | 21 |
| diethylcarbamazine | 32 |
| diprophylline | 11 |
| D-mannose | 18 |
| idebenone | 53 |
| ifenprodil | 28 |
| levosimendan | 20 |
| mexiletine | 10 |
| nicergoline | 40 |
| piribedil | 24 |
| tolfenamic acid | 9 |
| tolperisone | 19 |
| torasemide | 16 |
| triamterene | 18 |
| rilmenidine | 16 |

The efficacy of drug combinations of the invention is also assessed in the above in vitro models. The protocol used in these assays is the same as described in section 1 above. The drug combinations listed in Table 5 below show a particularly high relative performance value (determined as above).

Results:

All the drug combinations detailed in Table 5, led to a global positive effect for the normalization of blood glucose level, and are thus considered as efficient in the treatment of diabetes.

TABLE 5

| Drug combinations with a high relative value | Efficacy in diabetes |
| --- | --- |
| Ifenprodil and acamprosate | + |
| Ifenprodil and baclofen | + |
| baclofen and acamprosate | + |
| mexiletine and cinacalcet | + |
| mexiletine and torasemide | + |
| sulfisoxazole and torasemide | + |
| azelastine and nicergoline | + |
| idebenone and nicergoline | + |
| carbetapentane and nicergoline | + |
| almitrine and nicergoline | + |
| cimetidine and nicergoline | + |
| diethylcarbamazine and nicergoline | + |
| ifenprodil and nicergoline | + |
| azelastine and idebenone | + |
| acamprosate and nicergoline | + |
| azelastine and carbetapentane | + |
| azelastine and almitrine | + |
| idebenone and carbetapentane | + |
| idebenone and almitrine | + |
| triamterene and nicergoline | + |
| D-mannose and nicergoline | + |
| idebenone and diethylcarbamazine | + |
| baclofen and D-mannose | + |
| baclofen and metformin | + |
| D-mannose and metformin | + |
| baclofen and D-mannose and metformin | + |
| ifenprodil and fenspiride | + |
| ifenprodil and torasemide | + |
| ifenprodil and triamterene | + |
| ifenprodil and tolfenamic acid | + |
| fenspiride and torasemide | + |
| fenspiride and triamterene | + |
| fenspiride and tolfenamic acid | + |
| torasemide and triamterene | + |
| torasemide and tolfenamic acid | + |
| triamterene and tolfenamic acid | + |
| metformin and torasemide | + |
| metformin and triamterene | + |
| metformin and tolfenamic acid | + |
| metformin and ifenprodil and fenspiride | + |
| metformin and ifenprodil and torasemide | + |
| metformin and ifenprodil and triamterene | + |
| metformin and ifenprodil and tolfenamic acid | + |
| metformin and fenspiride and torasemide | + |
| metformin and fenspiride and triamterene | + |
| metformin and fenspiride and tolfenamic acid | + |
| metformin and torasemide and triamterene | + |
| metformin and torasemide and tolfenamic acid | + |
| metformin and triamterene and tolfenamic acid | + |

2. In Vivo Studies 2.1 Anti-Inflammatory Effect of Combinations in Zucker Diabetic Fatty (ZDF) Rat Model The efficacy of drug compositions of the invention comprising the compound(s) of Tables 4 and 5 is confirmed in the Zucker Diabetic Fatty (ZDF) rat model. The Zucker Diabetic Fatty (ZDF) rat is an accurate model for type 2 diabetes based on impaired glucose tolerance caused by the inherited obesity gene mutation which leads to insulin resistance. The fa mutation, which occurs in ZDF rat, results in shortened leptin receptor protein which does not effectively interact with leptin. This mutation is phenotypically expressed as obesity with high levels of normal leptin in the blood.

It is known that inflammation plays a role in the etiology of type 2 diabetes and metabolic syndrome. Abnormal high plasmatic levels of C reactive protein (CRP) are associated with diabetes and metabolic syndrome. ZDF rats have been used to study the effect of compositions of the invention on inflammatory component of type 2 diabetes. ZDF rats show an increased level of plasmatic CRP.

Husbandry and Chronic Treatment

Rats were housed individually and kept at 22+/−2° C. on a 12-h light/dark cycle. Animals had access to food (Purina 5008) and water ad libitum. Whereas one group received the vehicle, the other groups were treated with the candidate compounds listed in tables 5 and 6 during 4 weeks. Administrations were performed twice a day by oral route.

Blood Samples

Blood samples were taken from the topically anaesthetized tails of overnight-fasted rats in all groups.

Measurement of Plasma CRP Level

The CRP concentration in the plasma of all rats (Lean rats, vehicle, and baclofen-acamprosate treated ZDF rats) were measured by an ELISA kit according to the manufacturer recommendations (ref CYT294 from Millipore). The rat C-Reactive Protein (CRP) kit is a double polyclonal antibody sandwich enzyme immunoassay (HA), which measures rat CRP. Standards, quality controls and samples of plasma were incubated for 30 min in microtitration wells coated with polyclonal anti-rat CRP antibody. After a thorough wash, polyclonal anti-rat CRP antibody labelled with horseradish peroxidase (HRP) was added to the wells and incubated for 30 minutes with the immobilized antibody-CRP complex. Following another washing step, the remaining HRP-conjugated antibody was allowed to react with the substrate and tetramethylbenzidine (TMB). The reaction (5-10 min) was stopped by addition of an acidic solution, and absorbance of the resulting yellow color product was measured spectrophotometrically at 450 nm. The absorbance is proportional to the concentration of CRP. A standard curve was constructed by plotting absorbance values versus CRP concentrations of standards, and concentrations of unknown samples were determined using this standard curve.

Results

Figure 22:
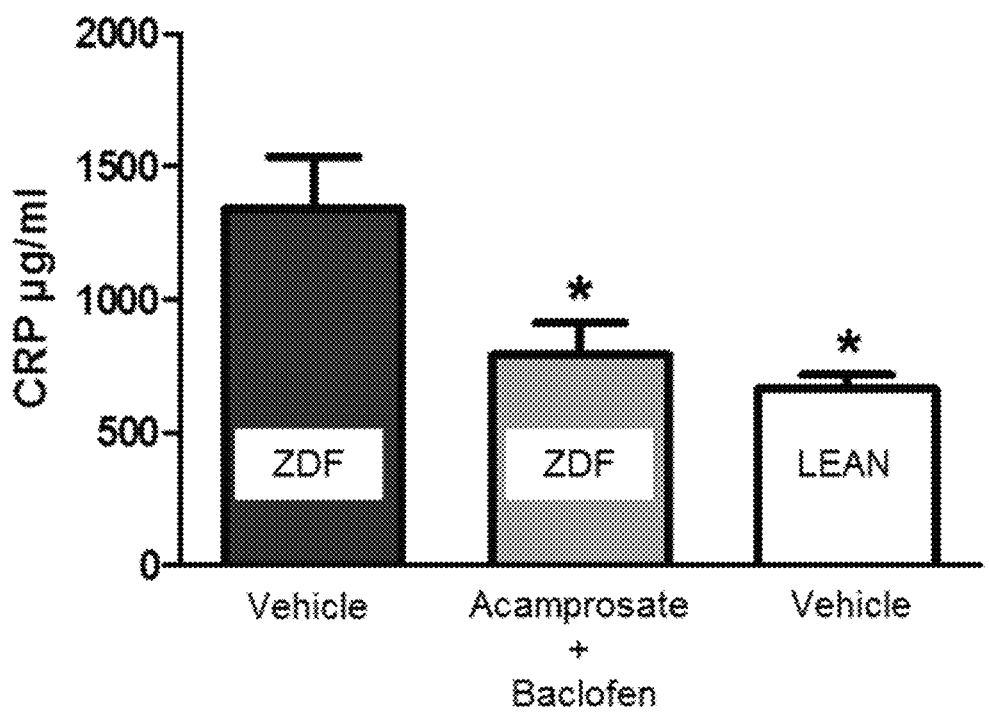
FIG. 22: Effect of baclofen-acamprosate combination on plasma CRP concentration in ZDF male rats after a 4-week treatment. The CRP concentration is significantly reduced by baclofen-acamprosate combination in treated ZDF rats when compared to non-treated ZDF rats.

Compositions of the invention are efficient in reducing CRP concentration in the plasma of ZDF rats. For example, FIG. 22 shows that the CRP concentration is significantly reduced by—acamprosate and baclofen treatment (7.5 mg/kg and 0.5 mg/kg respectively) when compared to vehicle-treated ZDF rats, and reaches the CRP level of lean rats. Those results suggest a systemic anti-inflammatory effect of combinations of the invention.

2.2 Glucose Homeostasis Control in Db/Db Mice Model

The strain db/db mouse, deficient in leptin receptor, is a well-known and characterized mouse model used to evaluate compounds targeting diabetes. db/+ heterozygotous mouse was used as control.

Acclimatization and Pre-Study Periods 85 mice (8-week old, 75 db/db and 10 db/+) were purchased from Janvier (France). Animals were housed in 28 ventilated cages (530 cm$^2$×20 cm) throughout the experimental phase. Animals' beddings were renewed twice a week. Small devices were placed in the cages for enrichment of environment (mouse houses and cellulose plugs). Mice were housed in groups of 2 animals with a normal 12 hour light cycle (lights off at 07:00 pm), 22±2° C. and 55±10% relative humidity. Mice had at least 14 days of acclimatization during which mice were fed with a standard chow R04 diet (SAFE-Augy France) and had free access to water.

After 12 days of acclimatization and 2 days (DO) before the beginning of the treatments, all mice were weighed and fasted for 6-hours from 08:00 am to 02:00 pm. Subsequently, body weight has been measured daily all along the study.

Blood (200 µL/EDTA) was collected from the retro bulbar sinus under isoflurane anesthesia. Plasma glucose and plasma insulin were quantified using enzymatic and immune-enzymatic methods respectively in order to randomize animals in homogenous groups.

At Day 0, just before the gavage, a drop of blood was collected from the tail vein to measure the non-fasted blood glucose using a glucometer (SmartCheck®).

Test Groups

Mice were allocated to groups according to their body weight and fasted blood glucose (N=8 mice/group):

Lean controls (db/+ mice) treated with vehicle (per os, twice daily).

Obese negative controls (db/db mice) treated with vehicle (per os, twice daily).

Obese positive controls (db/db mice) treated with metformin at 300 mg/kg (per os, once daily).

Obese animals (db/db mice) treated with compounds or compositions of the invention.

Treatment

The treatment study duration was 6 weeks. Mice were treated twice daily at 08:00 am and at 04:00 pm by gavage with vehicle, reference compound or PXT compounds in respect of the following ratio: 10 mL/kg dosing (up to 20 mL/kg/day max).

Gavage volumes have been adjusted individually to the body weight recorded in the morning.

During the treatment period, food and water consumption were monitored and recorded. Food intake was measured and recorded daily (difference between two consecutive days). The mean food intake expressed as grams of food consumed per animal per day were assigned to all the mice of the considered cage. Water intake was evaluated twice a week using the same method.

Once a week, at Days D7, D13, D21, D27, D35 and D41 just before the gavage, a drop of blood was collected from the tail vein to measure the non-fasted blood glucose using a glucometer (SmartCheck®).

At Days D14, D28 and D42, food was removed at 08:00 am. Blood (200 µL/EDTA) was collected from the retro bulbar sinus under anesthesia at 02:00 pm (after 6 hours of fasting) to measure fasting plasma glucose.

Glucose Quantification

Plasma glucose concentration was determined by a colorimetric method based on enzymatic oxidation of glucose in the presence of glucose oxidase. The produced hydrogen peroxide reacts with phenol and 4-aminophenazone in a reaction catalyzed by peroxidase to form a red-violet quinoneimine dye as indicator. The intensity of the final color is directly proportional to the glucose concentration and was measured at 505 nm.

Results

Figure 23:
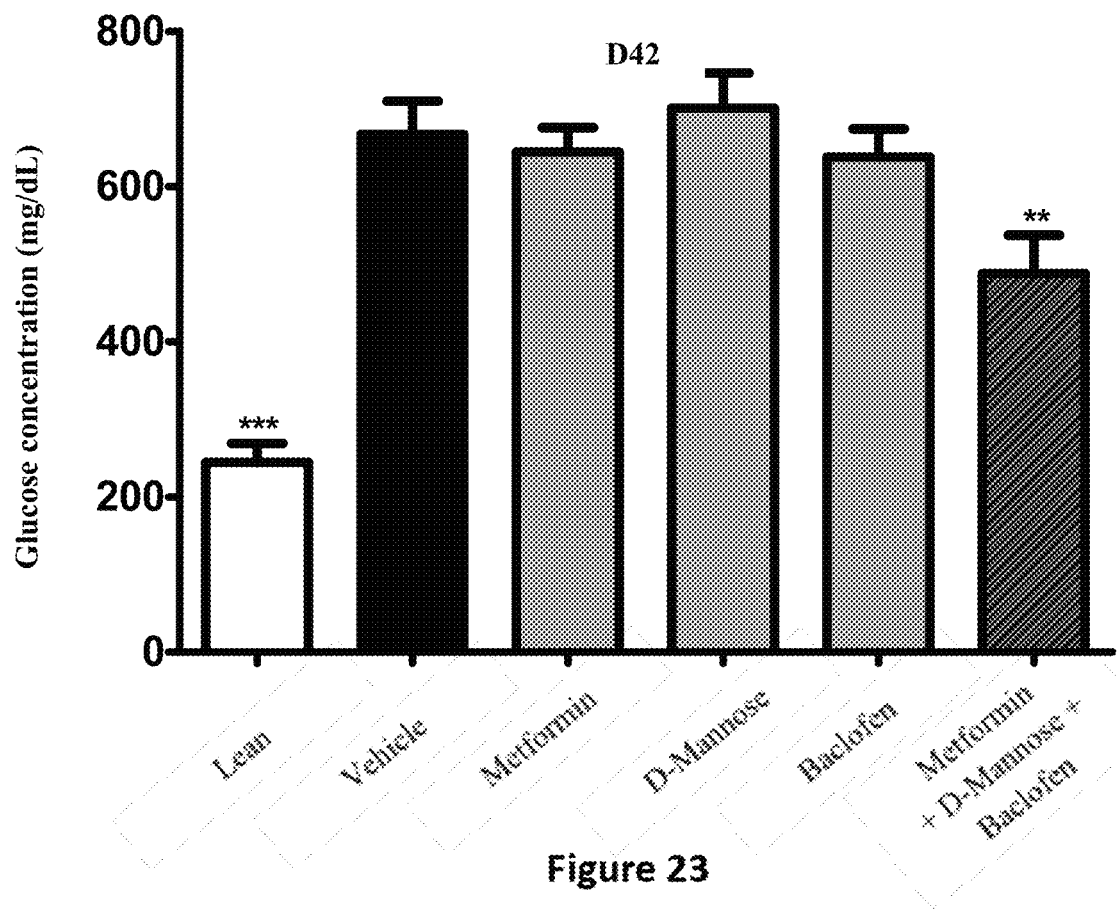
FIG. 23: Effect of D-mannose-baclofen-metformin combination (respectively, 5 mg/kg and 2 mg/kg bid, and 150 mg/kg once day) short term treatment on glucose homeostasis in db/db mice. Fasting glycaemia (mg/dL) is significantly decreased in treated db/db mice, when compared with non-treated db/db mice.
Figure 24:
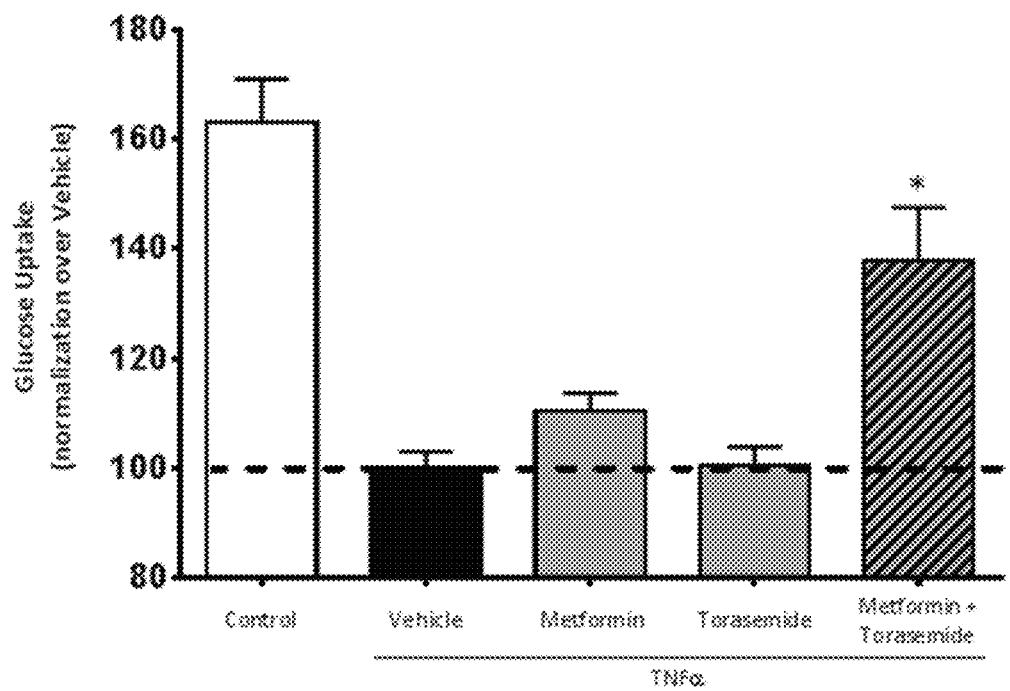
FIG. 24: Enhancing effect of torasemide on the treatment of insulin resistance with metformin in the model of glucose uptake in 3T3L1 differentiated adipocytes, under TNF-α induced insulin resistance conditions. Glucose uptake is significantly enhanced (+138%) in insulin resistant cells pretreated with a combination of the two drugs (hatch bar, torasemide 10 nM and metformin 250 µM) when compared to the non-treated insulin resistant cells (black bar). No significant effect is noticed for the drugs when used alone at the same concentrations (grey bars, Dunnett's test, *p<0.05).
Figure 25:
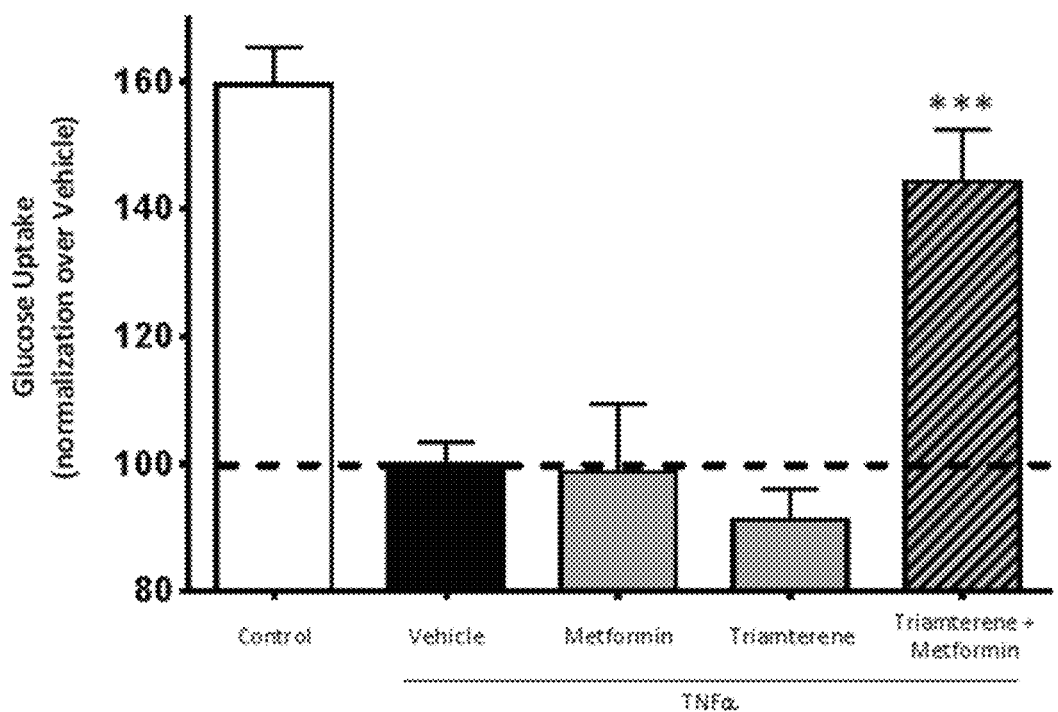
FIG. 25: Enhancing effect of triamterene on the treatment of insulin resistance with metformin in the model of glucose uptake by 3T3L1 differentiated adipocytes, under TNF-α induced insulin resistance conditions. Glucose uptake is significantly enhanced (+144%) in insulin resistant cells pretreated with the combination of the two drugs (hatch bar, triamterene 3.3 nM and metformin 100 µM) when compared to the non-treated insulin resistant cells (black bar). No significant effect is noticed for the drugs when used alone at the same concentrations (grey bars, Dunnett's test, ***p<0.001).
Figure 26:
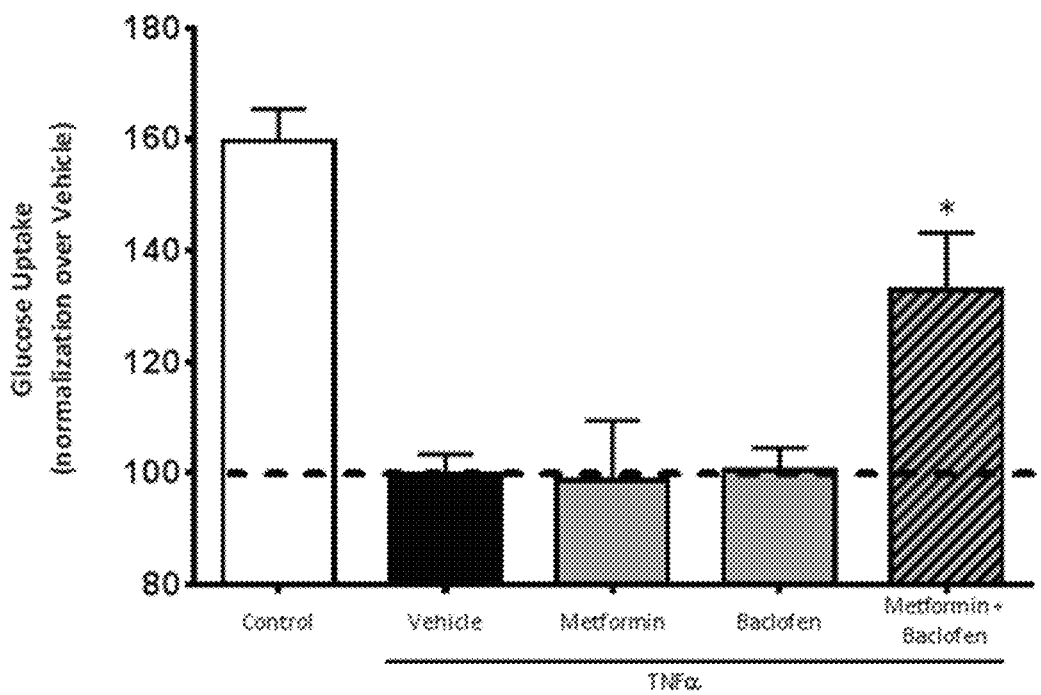
FIG. 26: Enhancing effect of baclofen on the treatment of insulin resistance with metformin in the model of glucose uptake by 3T3L1 differentiated adipocytes, under TNF-α induced insulin resistance conditions. Glucose uptake is significantly enhanced (+133%) in insulin resistant cells pretreated with the combination of the two drugs (hatch bar, baclofen 3.3 nM and metformin 100 µM) when compared to the non-treated insulin resistant cells (black bar). No significant effect is noticed for the drugs when used alone at the same concentrations (grey bars, Dunnett's test, *p<0.05).
Figure 27:
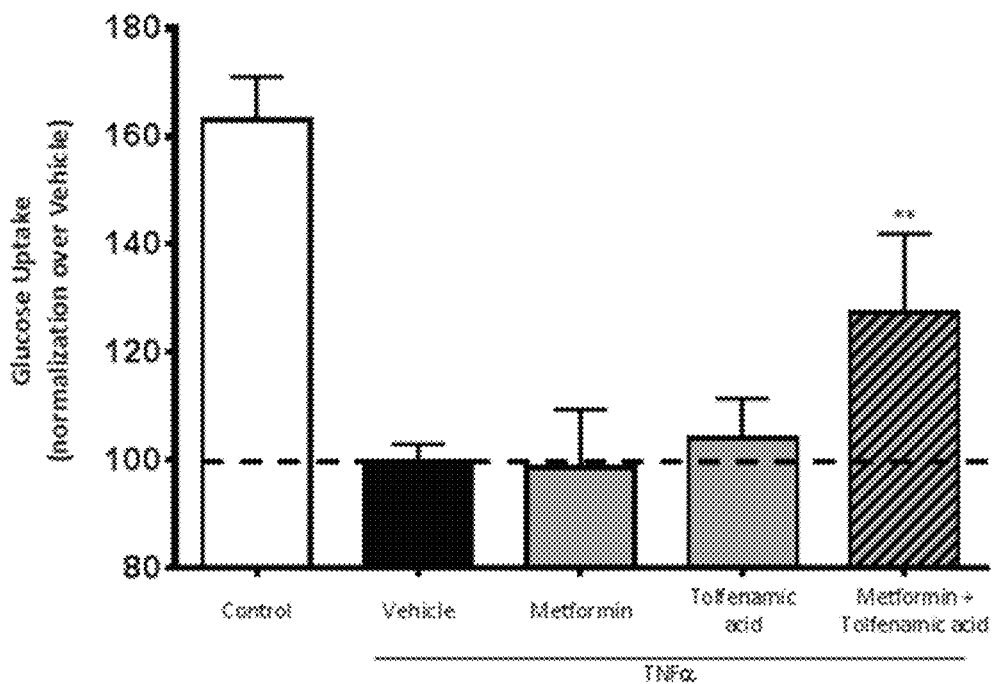
FIG. 27: Enhancing effect of tolfenamic acid on the treatment of insulin resistance with metformin in the model of glucose uptake by 3T3L1 differentiated adipocytes, under TNF-α induced insulin resistance conditions. Glucose uptake is significantly enhanced (+127%) in insulin resistant cells pretreated with the combination of the two drugs (hatch bar, tolfenamic acid 3.3 nM and metformin 100 µM) when compared to the non-treated insulin resistant cells (black bar). No significant effect is noticed for the drugs when used alone at the same concentrations (grey bar, t test, **p<0.01).

Compositions of the invention reduce glycaemia in the plasma of db/db mice as soon as D28 of treatment (not shown). FIG. 23 shows that at D42, the glucose concentration is significantly reduced by administration of a combination of D-mannose (5 mg/kg), (RS)-baclofen (6 mg/kg) and metformin (150 mg/kg) when compared with vehicle administered animals (p<0.001).

Noteworthy, the drugs, when used alone, do not induce any significant lowering of glycaemia. More remarkably, compounds of the invention can be considered as potent enhancers of currently known treatment for diabetes, thereby allowing the reduction of dosages and thus expecting a lowering of side effects.

REFERENCES 1. van Belle, T. L., K. T. Coppieters, and M. G. von Herrath, *Type 1 diabetes: etiology, immunology, and therapeutic strategies*. Physiol Rev, 2011. 91(1): p. 79-118.

2. Maggio, C. A. and F. X. Pi-Sunyer, *The prevention and treatment of obesity. Application to type 2 diabetes.* Diabetes Care, 1997. 20(11): p. 1744-66.
3. Stumvoll, M., B. J. Goldstein, and T. W. van Haeften, *Type 2 diabetes: principles of pathogenesis and therapy.* Lancet, 2005. 365(9467): p. 1333-46.
4. Boden, G., *Role of fatty acids in the pathogenesis of insulin resistance and NIDDM.* Diabetes, 1997. 46(1): p. 3-10.
5. Goldstein, B. J., *Insulin resistance as the core defect in type 2 diabetes mellitus.* Am J Cardiol, 2002. 90(5A): p. 3G-10G.
6. Bessac, L., *Unmet medical needs and therapeutic goals in the treatment of type 2 diabetes.* Curr Opin Investig Drugs, 2003. 4(10): p. 1173-8.
7. Rolla, A. R., *Starting insulin strategies for patients with an inadequate response to oral therapy.* Diabetes Obes Metab, 2009. 11 Suppl 5: p. 6-9.
8. Yang, Y. X., S. Hennessy, and J. D. Lewis, *Insulin therapy and colorectal cancer risk among type 2 diabetes mellitus patients.* Gastroenterology, 2004. 127(4): p. 1044-50.
9. Nathan, D. M., et al., *Medical management of hyperglycemia in type 2 diabetes: a consensus algorithm for the initiation and adjustment of therapy: a consensus statement of the American Diabetes Association and the European Association for the Study of Diabetes.* Diabetes Care, 2009. 32(1): p. 193-203.
10. Ettmayer, P., Amidon, G. L., Clement, B. & Testa, B. Lessons learned from marketed and investigational prodrugs. *J. Med. Chem.* 47, 2393-2404 (2004).
11. Beaumont, K., Webster, R., Gardner, I. & Dack, K. Design of ester prodrugs to enhance oral absorption of poorly permeable compounds: challenges to the discovery scientist. *Curr. Drug Metab.* 4, 461-485 (2003).
12. Heimbach, T. et al. Enzyme-mediated precipitation of parent drugs from their phosphate prodrugs. *Int. J. Pharm.* 261, 81-92 (2003).
13. Yang, C. Y., Dantzig, A. H. & Pidgeon, C. Intestinal peptide transport systems and oral drug availability. *Pharm. Res.* 16, 1331-1343 (1999).
14. Steffansen, B. et al. Intestinal solute carriers: an overview of trends and strategies for improving oral drug absorption. *Eur. J. Pharm. Sci.* 21, 3-16 (2004).
15. Stella, V. et al. Prodrugs: Challenges and Rewards (AAPS, New York, 2007).
16. Wermuth, C G. The Practice of Medicinal Chemistry. (Hardbound, 2003). Part VI, Chap 33: Designing prodrugs and bioprecursors.
17. Pezron, I. et al. Prodrug strategies in nasal drug delivery. *Expert Opin. Ther. Pat.*, Vol. 12, No. 3, 331-340 (2002).
18. Stella, V. J. Prodrugs as therapeutics. *Expert Opin. Ther. Pat.* 14, 277-280 (2004).
19. Stella, V. J. & Nti-Addae, K. W. Prodrug strategies to overcome poor water solubility. *Adv. Drug Deliv. Rev.* 59, 677-694 (2007).
20. Higuchi, T.; Stella, V. eds. Prodrugs As Novel Drug Delivery Systems. *ACS Symposium Series.* American Chemical Society: Washington, D.C. (1975). 31.
21. Roche, E. B. Design of Biopharmaceutical Properties through Prodrugs and Analogs. American Pharmaceutical Association: Washington, D.C. (1977).
22. Stahl H., Wermuth C. G. (Eds.) Handbook of *Pharmaceutical Salts*: Properties, Selection, and Use. Wiley-VCH; 2 edition (Mar. 29, 2011).
23. Asfari M., Janjic D., Meda P., Li G., Halban P. A., and Wollheim C. B. Establishment of 2-mercaptoethanol-dependent differentiated insulin-secreting cell lines. *Endocrinology* 130: 167-78; (1992).
24. Frankfurt O. S. and Krishan A. Enzyme-linked immunosorbent assay (ELISA) for the specific detection of apoptotic cells and its application to rapid drug screening. *J Immunol Methods* 253:133-144 (2001).
25. Fryer L. G., Hajduch E., Rencurel F., Salt I. P., Hundal H. S., Hardie D. G., Carling D. Activation of glucose transport by AMP-activated protein kinase via stimulation of nitric oxide synthase. *Diabetes.* December; 49(12): 1978-85. (2000).

We claim:
1. A method for treating a mammalian subject having diabetes or a related disorder selected from impaired glucose tolerance, impaired fasting glucose, insulin resistance, metabolic syndrome, postprandial hyperglycemia and/or overweight/obesity comprising administering to said subject an effective amount of (i) at least one compound selected from levosimendan, almitrine, azelastine, carbetapentane, cinacalcet, dexbrompheniramine, diethylcarbamazine, D-mannose, nicergoline, tolfenamic acid, tolperisone, torasemide or triamterene, or salt(s) or sustained release formulation(s) thereof, in combination with (ii) metformin or salt(s) or sustained release formulation(s) thereof, wherein the effective amount is an effective amount in the assay of protective effect against apoptosis of beta cells, normalization of blood glucose level and/or glucose uptake by adipocyte under insulin resistance condition, with the proviso that said method does not comprise the administration of fenspiride and/or ifenprodil.

2. The method of claim 1, wherein the method comprises administering at least one of the following combinations of compounds:
torasemide and metformin,
triamterene and metformin, or
tolfenamic acid and metformin
or salt(s) or sustained release formulation(s) thereof.

3. The method of claim 1, wherein the method comprises administering at least one of the following combinations of compounds:
azelastine and nicergoline,
carbetapentane and nicergoline,
almitrine and nicergoline,
diethylcarbamazine and nicergoline,
azelastine and carbetapentane,
azelastine and almitrine,
triamterene and nicergoline,
D-mannose and nicergoline,
torasemide and tolfenamic acid,
torasemide and triamterene, or
tolfenamic acid and triamterene,
or salt(s) or sustained release formulation(s) thereof, in combination with metformin or a salt or sustained release formulation thereof.

4. A method for controlling blood glucose level in a mammalian subject in need thereof, comprising administering to said subject a combination of (i) and (ii) as defined in claim 1.

5. A method for increasing or stimulating glucose uptake in adipocytes and/or muscular cells in a mammalian subject in need thereof, comprising administering to said subject a combination of (i) and (ii) as defined in claim 1.

6. A method for decreasing apoptosis of pancreatic beta cells in a mammalian subject in need thereof, comprising administering to said subject a combination of (i) and (ii) as defined in claim 1.

7. The method of claim 1, wherein the subject has type 2 diabetes.

8. The method of claim 1, wherein said combination is administered repeatedly to the subject.

9. The method of claim 1, wherein the compounds in said combinations are formulated for a simultaneous, sequential or separate administration to the subject.

10. The method of claim 1, wherein the compounds in said combination are formulated in a single composition.

11. The method of claim 1, wherein said combination further comprises a pharmaceutically acceptable carrier or excipient.

12. The method of claim 4, wherein the subject has type 2 diabetes.

13. The method of claim 5, wherein the subject has type 2 diabetes.

14. The method of claim 6, wherein the subject has type 2 diabetes.

15. The method of claim 4, wherein said combination is administered repeatedly to the subject.

16. The method of claim 5, wherein said combination is administered repeatedly to the subject.

17. The method of claim 6, wherein said combination is administered repeatedly to the subject.

18. The method of claim 4, wherein the compounds in said combinations are formulated for a simultaneous, sequential or separate administration to the subject.

19. The method of claim 4, wherein the compounds in said combination are formulated in a single composition.

20. The method of claim 4, wherein said combination further comprises a pharmaceutically acceptable carrier or excipient.

* * * * *

UNITED STATES PATENT AND TRADEMARK OFFICE
CERTIFICATE OF CORRECTION

PATENT NO. : 10,617,689 B2
APPLICATION NO. : 15/142227
DATED : April 14, 2020
INVENTOR(S) : Daniel Cohen et al.

Page 1 of 1

It is certified that error appears in the above-identified patent and that said Letters Patent is hereby corrected as shown below:

In the Specification

Column 32,
Line 37, "in FIBS" should read --in HBS--.

Signed and Sealed this
Eighteenth Day of August, 2020

Andrei Iancu
*Director of the United States Patent and Trademark Office*